(12) United States Patent
Stuckey

(10) Patent No.: US 11,436,934 B2
(45) Date of Patent: Sep. 6, 2022

(54) SYSTEMS AND METHODS FOR PROVIDING A DIALOG ASSESSMENT PLATFORM

(71) Applicant: Inquiry Technologies, LLC, London, KY (US)

(72) Inventor: Scott E. Stuckey, London, KY (US)

(*) Notice: Subject to any disclaimer, the term of this patent is extended or adjusted under 35 U.S.C. 154(b) by 0 days.

(21) Appl. No.: 17/369,564

(22) Filed: Jul. 7, 2021

(65) Prior Publication Data
US 2022/0013025 A1 Jan. 13, 2022

Related U.S. Application Data

(60) Provisional application No. 63/049,435, filed on Jul. 8, 2020.

(51) Int. Cl.
*G09B 5/00* (2006.01)
*G09B 5/06* (2006.01)
(Continued)

(52) U.S. Cl.
CPC ......... *G09B 5/065* (2013.01); *G06F 3/04842* (2013.01); *G06F 40/30* (2020.01); *G06N 5/04* (2013.01); *G06Q 10/06311* (2013.01); *G06Q 10/06398* (2013.01); *G06Q 50/2057* (2013.01); *G09B 5/04* (2013.01); *G09B 19/04* (2013.01);
(Continued)

(58) Field of Classification Search
CPC ........... G09B 5/06; G09B 5/065; G06F 3/048; G06F 40/169
See application file for complete search history.

(56) References Cited

U.S. PATENT DOCUMENTS 8,266,068 B1 9/2012 Foss et al.
11,093,901 B1 * 8/2021 Preuss ................... G06F 40/242
(Continued)

FOREIGN PATENT DOCUMENTS

KR 101375119 B1 3/2014
KR 20200008838 A 1/2020

OTHER PUBLICATIONS

Form 2 and Complete Specification believed to be Indian Application No. 201741024306A, entitled "A virtual interview and advisory system for assessment and enhancement of skills or personal development", by applicant Sai Ujwal Surampalli et al.
(Continued)

*Primary Examiner* — Peter R Egloff
(74) *Attorney, Agent, or Firm* — Dinsmore & Shohl LLP

(57) ABSTRACT

One embodiment includes a processor and a memory component coupled to the processor. The memory component stores logic that, when executed by the processor, causes the system to provide a first user interface for a trainee to practice a skill, receive a first recording from the trainee practicing the skill, provide the first recording to a trainer, and provide a second user interface for the trainer to provide comments to the first recording. In some embodiments, the logic causes the system to receive a comment from the trainer at a first section of the first recording, save the comment as a previously recorded comment, perform an analysis of the first recording to determine a feature of the interaction that corresponds to the previously recorded comment, and predict when the trainer will provide the previously recorded comment to a second section of the recording, based on the analysis of the feature.

20 Claims, 17 Drawing Sheets

(51) Int. Cl.

| | | |
|---|---|---|
| *G11B 27/036* | (2006.01) | |
| *G06F 3/04842* | (2022.01) | |
| *G06F 40/30* | (2020.01) | |
| *G09B 19/04* | (2006.01) | |
| *G06Q 50/20* | (2012.01) | |
| *G06Q 10/06* | (2012.01) | |
| *G06N 5/04* | (2006.01) | |
| *G09B 5/04* | (2006.01) | |
| *G16H 40/20* | (2018.01) | |
| *G06Q 10/10* | (2012.01) | |

(52) U.S. Cl.
CPC ....... *G11B 27/036* (2013.01); *G06Q 10/1053* (2013.01); *G16H 40/20* (2018.01)

(56) References Cited

U.S. PATENT DOCUMENTS

| | | | |
|---|---|---|---|
| 2002/0146667 A1* | 10/2002 | Dowdell | G09B 7/02 434/62 |
| 2004/0186743 A1 | 9/2004 | Cordero, Jr. | |
| 2007/0088601 A1* | 4/2007 | Money | G09B 7/02 705/321 |
| 2008/0086504 A1 | 4/2008 | Sanders et al. | |
| 2008/0147585 A1* | 6/2008 | Lacey | G09B 7/00 706/47 |
| 2013/0226578 A1* | 8/2013 | Bolton | G06Q 10/1057 704/235 |
| 2014/0236850 A1 | 8/2014 | Holland | |
| 2014/0308646 A1* | 10/2014 | Wurth | G09B 7/04 434/350 |
| 2015/0043657 A1 | 2/2015 | Choi et al. | |
| 2017/0213190 A1* | 7/2017 | Hazan | G06Q 10/1053 |
| 2018/0122252 A1* | 5/2018 | Zhang | G09B 5/06 |
| 2018/0165979 A1* | 6/2018 | Correia Gracio | G06Q 10/06398 |
| 2019/0198011 A1 | 6/2019 | Kerr et al. | |

OTHER PUBLICATIONS

International Search Report and Written Opinion issued in corresponding PCT Patent Application No. PCT/US2021/040838, dated Oct. 14, 2021.
https://www.interviewbuddy.in "Virtual face-to-face mock interviews with industry experts", accessed Sep. 10, 2020.
https://www.myinterviewpractice.com "Being prepared feels great!", accessed Sep. 11, 2020.

* cited by examiner

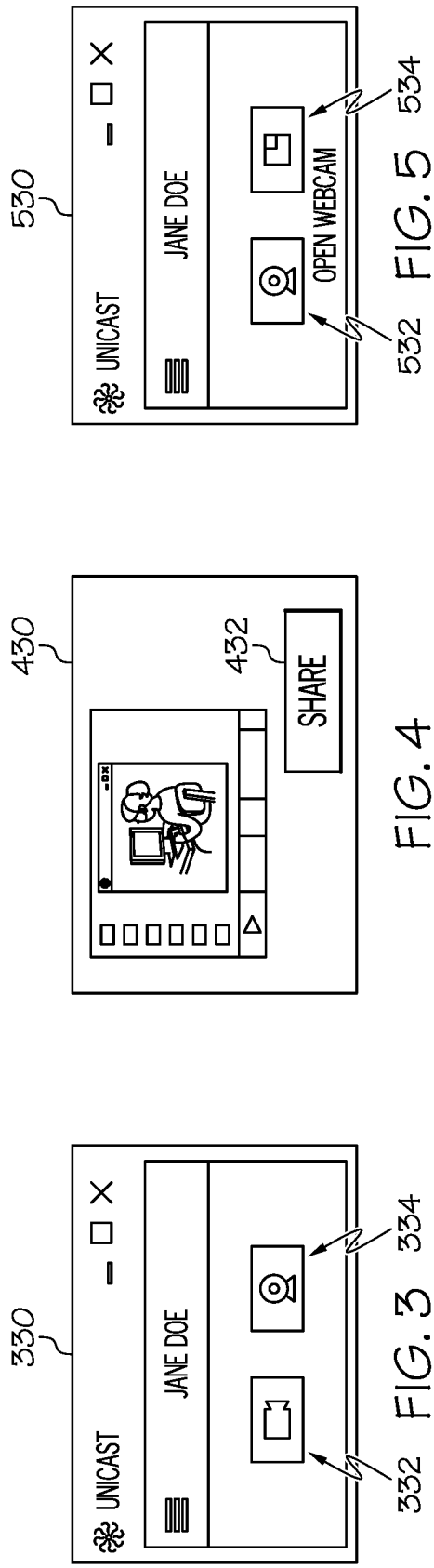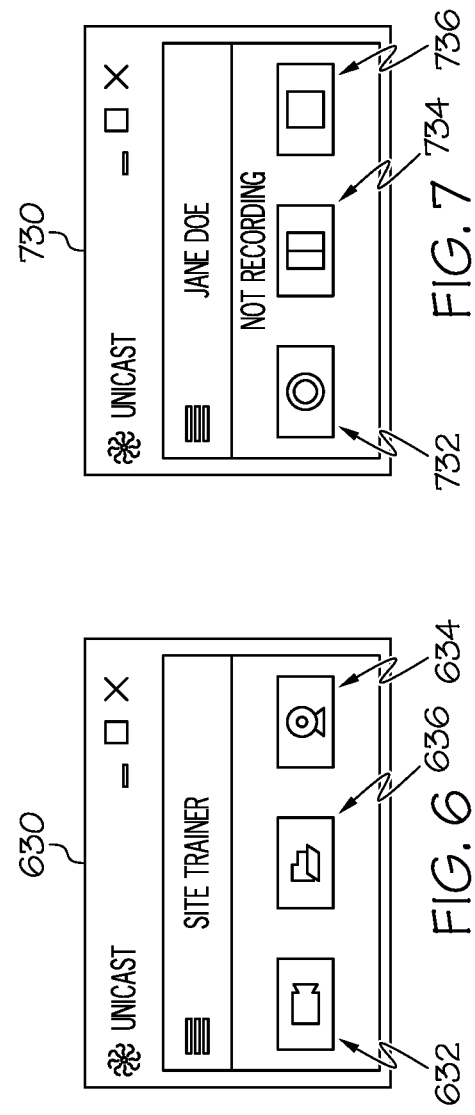

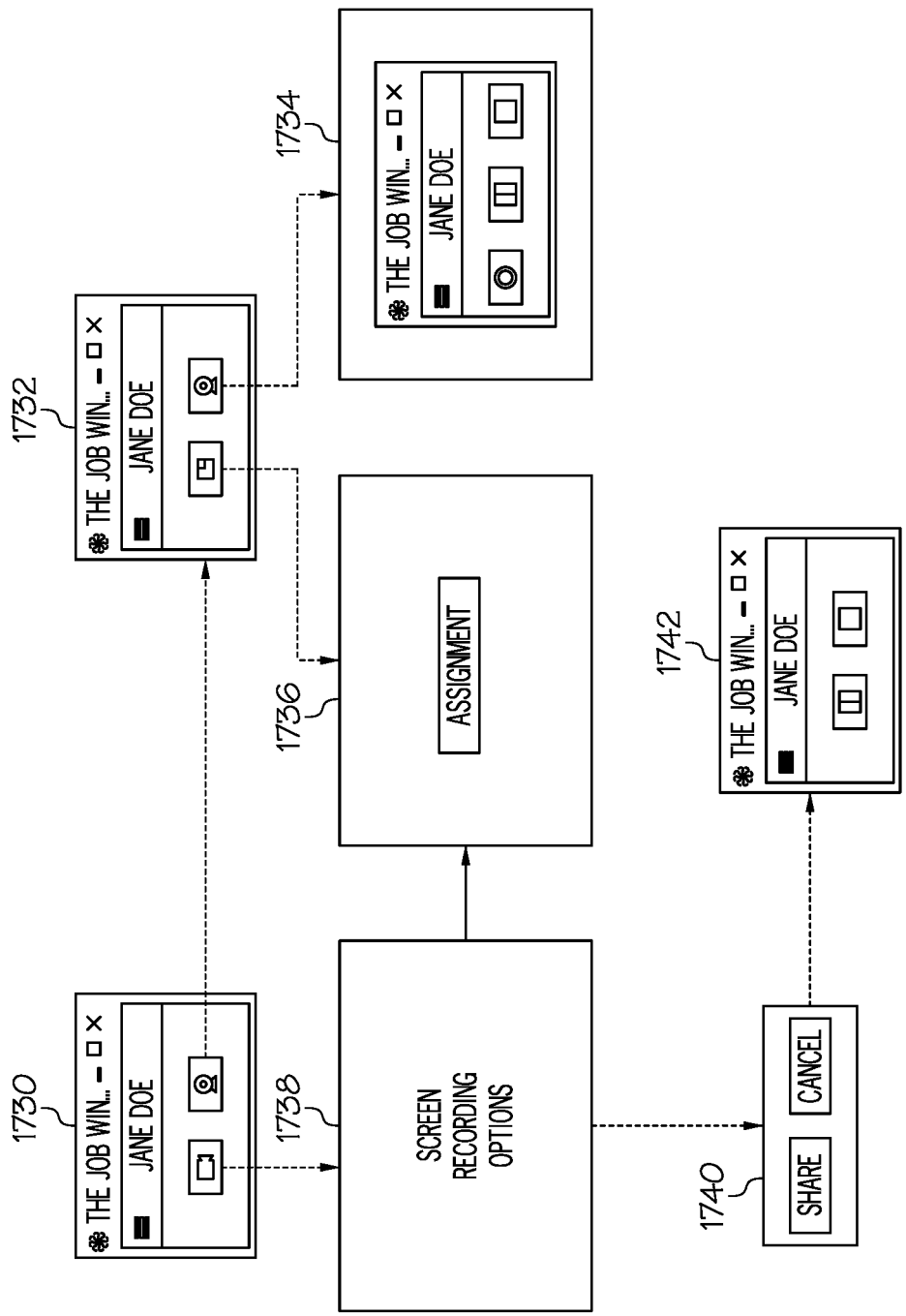

SYSTEMS AND METHODS FOR PROVIDING A DIALOG ASSESSMENT PLATFORM

CROSS REFERENCE

This application claims the benefit of U.S. Provisional Application Ser. No. 63/049,435 filed Jul. 8, 2020, which is hereby incorporated by reference in its entirety.

TECHNICAL FIELD

Embodiments described herein generally relate to systems and methods for providing a dialog assessment platform and, more specifically, to embodiments for providing a platform for providing customized feedback to persons training for interviews and/or other skills.

BACKGROUND

Many educational systems continue to show a number of alarming trends, including lower student achievement, higher dropout rates, a declining tax base, poor parental support, and fewer school resources. As a result, many parts of America consistently produce far fewer scientists, doctors, and engineers, and they often struggle to fill positions that require a highly skilled, technology-savvy workforce. This skills gap is growing wider as roughly two-thirds of the job openings today require some education beyond high school. In addition, jobs that have historically only required a high school degree or less are quickly being supplanted by automation and artificial intelligence. In response, many states now supplement federal investments in career and technical education (CTE) with additional funding towards the betterment of the students, and improvement of the economic stability of their particular regions.

In response to these challenges, organizations, private industries, and government agencies are implementing various types of educational curriculum, apprenticeship programs, workforce development applications, and rehabilitation counseling, all of which share of common goal providing training to build and support a highly skilled and much needed labor pool. The majority of these current training opportunities focus on the attainment of performance-based skill sets; however, the assessment models used to measure proficiency often do not evaluate the actual skills being taught. Rather, standard assessment items tend to include multiple choice, true/false, or short answer essay questions, all of which indirectly measure the successful acquisition of specific performance skills. The ability to answer questions correctly about a skill or task does not always equate to the ability to execute the tasks that are associated with the question properly. Likewise, people with certain learning disabilities and those that struggle with literacy may lack the capacity to understand the question and/or may have difficulty conveying understanding through writing. However, they may be perfectly adept in performing the actual skill(s) associated with the assessment item. Further, the type of feedback that instructors can supply with these current solutions is often limited in scope and lacks the personalization needed to correct or modify behaviors effectively. Despite the limitations that these antiquated forms of methodology and assessment present, the way these training programs are designed and implemented remains largely unchanged due to a paucity of alternative methods. Thus, a need exists in the industry.

SUMMARY

Embodiments described herein include systems and methods for providing a dialog assessment platform. One embodiment of a method includes providing a first user interface for a trainee to practice a skill, where the first user interface provides an interaction with the trainee, receiving a first recording from the trainee practicing the skill, and determining whether the trainee has reviewed the first recording. In response to determining that the trainee has reviewed the first recording, the method includes providing the first recording to a trainer, providing a second user interface for the trainer to provide comments to the first recording, and receiving a comment from the trainer at a first section of the first recording. The method may also include saving the comment as a previously recorded comment, performing an analysis of the first recording to determine a feature of the interaction that corresponds to the previously recorded comment, and predicting when the trainer will provide the previously recorded comment to a second section of the recording, based on the analysis of the feature. Some embodiments include providing an option to the trainer to insert the previously recorded comment into at the second section and, in response to selection of the option, inserting the previously recorded comment at the second section.

One embodiment of a system includes a processor and a memory component coupled to the processor. The memory component stores logic that, when executed by the processor, causes the system to provide a first user interface for a trainee to practice a skill, wherein the first user interface provides an interaction with the trainee, receive a first recording from the trainee practicing the skill, provide the first recording to a trainer, and provide a second user interface for the trainer to provide comments to the first recording. In some embodiments, the logic causes the system to receive a comment from the trainer at a first section of the first recording, save the comment as a previously recorded comment, perform an analysis of the first recording to determine a feature of the interaction that corresponds to the previously recorded comment, and predict when the trainer will provide the previously recorded comment to a second section of the recording, based on the analysis of the feature. In some embodiments, the logic causes the system to provide an option to the trainer to insert the previously recorded comment into at the second section and in response to selection of the option, insert the previously recorded comment at the second section.

Embodiments of a non-transitory computer-readable medium include logic that, when executed by a computing device causes the computing device to provide a first user interface for a trainee to practice a skill, where the first user interface provides an interaction with the trainee, receive a first recording of the trainee practicing the skill, and provide the first recording to a trainer. In some embodiments, the logic causes the computing device to provide a second user interface for the trainer to provide recorded comments to the first recording, receive a recorded comment from the trainer at a first section of the first recording, and save the recorded comment as a previously recorded comment In some embodiments, the logic cause the computing device to perform an analysis of the first recording to determine a feature of the interaction that corresponds to the previously recorded comment, predict when the trainer will provide the previously recorded comment to a second section of the recording, based on the analysis of the feature, provide an option to the trainer to insert the previously recorded comment into at the second section, and in response to selection of the option, insert the previously recorded comment at the second section.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which:

FIG. 3 depicts a trainee user interface, according to embodiments provided herein;

FIG. 4 depicts another trainee user interface, according to embodiments provided herein;

FIG. 5 depicts a webcam user interface for a trainee, according to embodiments provided herein;

FIG. 6 depicts a trainer user interface, according to embodiments provided herein;

FIG. 7 depicts a recording user interface for a trainee, according to embodiments provided herein;

FIGS. 17A-17B depict a plurality of user interfaces for providing a dialog assessment platform, according to embodiments described herein;

DETAILED DESCRIPTION

Figure 1:
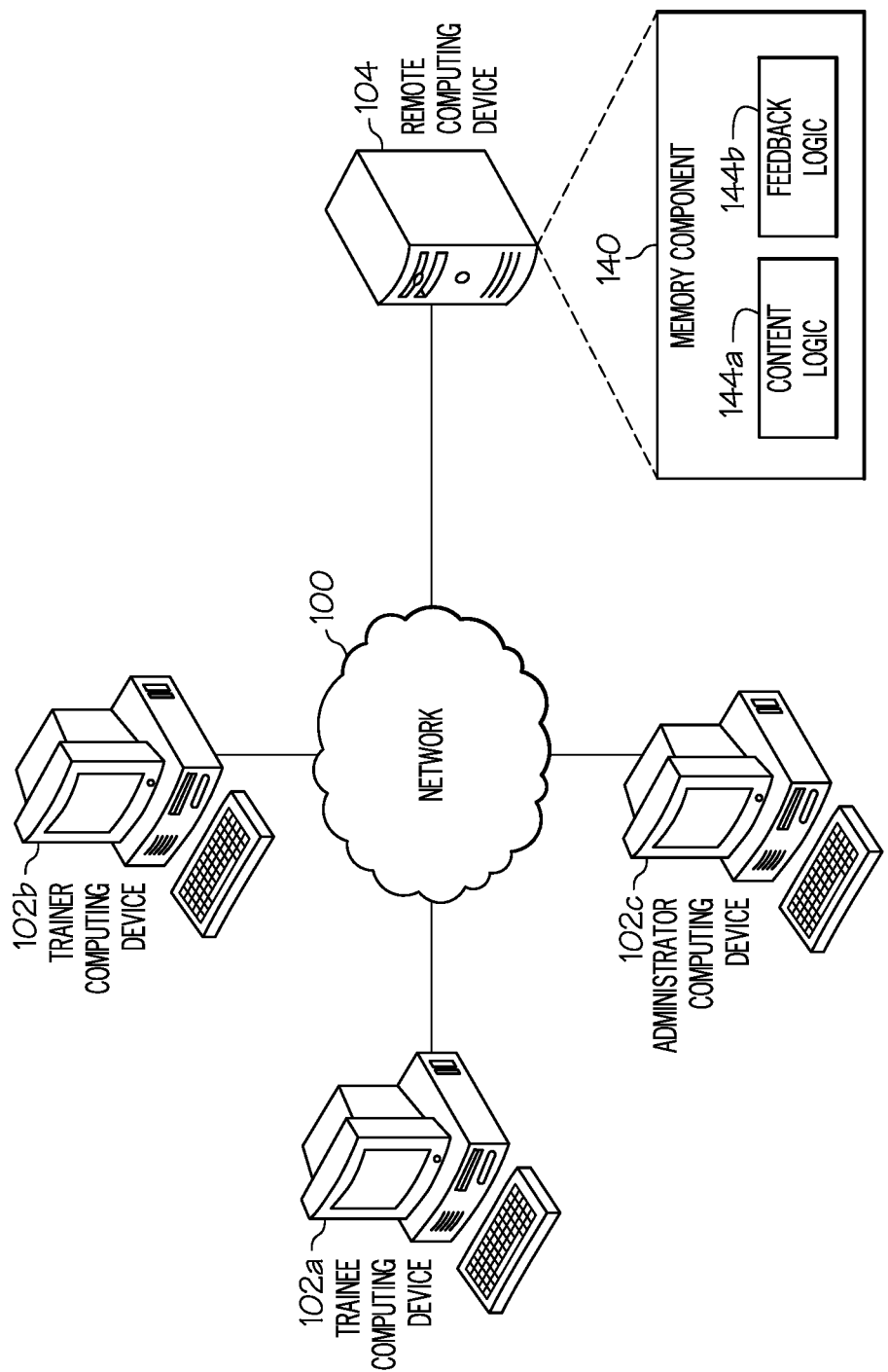
FIG. 1 depicts a computing environment for providing a dialog assessment platform, according to embodiments described herein.

Embodiments disclosed herein include systems and methods for providing a dialog assessment platform. Some embodiments are configured as an interview-training platform. In these embodiments, a job candidate may be provided virtual practice interviews with interview questions from a live (or simulated) interviewer. The trainee's answers may be recorded via a computing device camera, microphone, and/or other device and provided back to the trainee for self-review and/or critique. The video and/or audio may additionally be communicated to the instructor (or trainer), who may provide customized feedback on the trainee's responses, mannerisms, facial expressions, use of filler words, etc. The instructor may provide feedback via a spoken voice that may be separate from and/or overlaid over the interview video and/or audio content.

In some embodiments the instructor's comments may be at least one recorded comment (e.g., at least one audio clip and/or as at least one video clip) and compiled such that the instructor may "drag and drop" (or otherwise insert) the previously recorded comment in one or more locations in the interview recording without having to restate the same comment multiple times. Some embodiments may be configured to learn triggers for a particular instructor's comments and/or comments for a particular trainee such that suggestions may be automatically provided for inserting a comment. As an example, embodiments may learn that an instructor comments "reduce the filler words" every time the trainee says the word "um". These embodiments may be configured to determine instances that the trainee says the word "um" and prompt the instructor to insert the prerecorded comment at those points in the interview and/or automatically provided the comment. In addition to the customized feedback, some embodiments may provide a scale score or other scoring metric to track progress of the trainee objectively.

Specifically, these embodiments may be configured to analyze the words spoken, tone, volume, speed of speech, physical movements (such as posture, eye movement, etc.), as well as the number of comments, the variety of comments, and/or other of factors related to the comments provided by the trainer. Based on this analysis of the comments, and/or actions by the trainee, embodiments may determine a score for the recording. As an example, if the trainer uses the word "again," and rolls his/her eyes, these embodiments may detect that this is a comment that the trainer has made before and score that comment differently than a comment that was determined to only have occurred once. This analysis may be consolidated to one recording or may span several recordings (e.g., the trainer may review substance of all comments) to track improvement or degradation in the trainee's skills.

Similarly, some embodiments may be configured to require the trainee to review an interview before submitting to the instructor. These embodiments may create an obligation that the trainee provide his/her own feedback before requesting feedback from the instructor. As such, a self-evaluation process occurs in these embodiments prior to formal evaluation.

It should also be understood that while some embodiments are directed to interview skill training, this is merely one application. Some embodiments may be directed to negotiation skill training, customer service skill training, call center skill training, public speaking skill training, counseling skill training, K-12 skill training, higher education skill training, dialog skill training, interpersonal communication skill training, and/or other training. It will be understood that the user may be engaged in performance skills that do not require any spoken dialogue and/or use of the webcam feature. Examples could include a user engaged with a model, simulation, serious game, etc. Their actions performed on screen may still warrant a comment even without any spoken dialogue or visual display of the user engaged in the activity. These examples would include involve the use of a screen capture feature that captures the data on screen and may include audio spoken from the user.

Some embodiments provided herein are designed for organizations charged with helping others improve communication and soft-skills development of jobseekers seeking employment or improving their career status. These organizations include but are not limited to the job-services industry, human resource departments, and those involved with career and technical education (CTE). Until recently, both technical skills and soft skills were evaluated and scored during in-person job interviews. However, the hiring process for an increasing number of companies does not include dialogue with a real person. Many interviews are now conducted through video and scored by artificial intelligence (AI) algorithms. These algorithms may be implemented by a computer to analyze visual and grammatical cues and score each trainee on items like the number voice fillers, eye contact, rate of speech, and even what may appear in their background. Consequently, many qualified job candidates are being screened out, not based just on their technical skills, but for deficiencies in their soft skills.

Embodiments described herein utilize a wide variety of AI algorithms to target and flag for intervention specific areas within client videos that may warrant feedback for development of deficient interviewing skills. Instead of inserting digitized interventions, embodiments described herein may be prompted to relay corrective feedback as a voice-over comment that may be gently layered into the original client video. When the trainer voice-overs one of these feedback items, an option of tagging the audio file and saving it to a media library that is associated with the trainer's account may be provided. Then, when the AI analytics software causes the computing device to determine a need for that same intervention, the associated computing device retrieves the appropriate spoken comment from the trainer's audio library and either inserts it automatically or places it within the video timeline for review. The trainer may also add a personalized greeting such as "Hi Jane, I hope you're feeling better today" and a similar closing, thus leaving the trainee with the impression that they have had an in-depth review from a person they recognize. Thus, embodiments may provide insertion of a personalized intervention comment from the trainer.

Some embodiments may be configured to serve as a technical assistant that will analyze trainee videos for areas that may warrant intervention; communicate these findings to a trainer by marking specific points on a timeline within the performance video created by the trainee; and present data regarding the nature of the suggested intervention. The first time the need for a particular intervention is detected for any given evaluator, embodiments may suggest that the evaluator voice an audio comment that will be overlaid into the original video, tagged and stored in a media retrieval library that is specific to the evaluator. Then the next time these embodiments recognize the need for that intervention with the same or different trainee, the appropriate timeline is marked for review as before, but the previously recorded comment will have been retrieved and made available for inclusion within the original video. In some embodiments, deep fake alterations of the comment may be inserted to provide a more customized feel to identical comments made by the trainer.

In some embodiments, at the discretion of the organization, these pre-recorded audio feedback items can be fully inserted within trainee videos without having to be confirmed by the evaluator. Some embodiments may also support a hybrid model where the automatic placement of audio comments can be established by confidence levels associated with the actual analysis for each potential intervention. Those charged with training will be encouraged to also add highly personalized comments that address the specific trainee by name whenever possible. These unique comments can be used as greetings, moments of encouragement, or closing salutations.

The delivery of the various types of recording tools can be provided to any given user type. For example, only those that are involved with conducting evaluations have access to the feedback tool. Similarly, if an organization is solely interested in working with soft-skills development, then their clients would only need the webcam tool and not the screen recorder or picture-in-picture feature. It should be noted that users may include trainees, trainers, and/or administrators, depending on the particular context.

As such, some embodiments may be configured for tracking key points of human motion. Generally speaking, different algorithms excel at different aspects of human motions and multi-body part movement tracking algorithms tend to sacrifice robust performance on individual parts in order to capture a broader picture of its subject's movement. For example, one algorithm might efficiently track the arms, chest waist, legs, and feet at the cost of neglecting or poorly performing on the fingers, eyes, and facial features. To better diagnose interview performance, robustness of individual features are not be sacrificed for general "overall" movement.

In some embodiments, an analysis may be run on a user's motion and vocal utterances. These analyses may be combined into a larger framework that compiles these individual aspects into a single element for classification or training.

In some embodiments, feature extraction is intuitive, efficient, and pipelined for classification into a deep learning architecture. As such, these embodiments include a framework that locates the audiovisual information (e.g., an interview or student behavior), extracts features (e.g., iris movement, hand movement, body position, vocal formants, transcribed conversation, etc.) and flattens those extractions into a single testing element that can be provided to the deep learning architecture.

In some embodiments, datasets may be labelled prior to extraction, and classification for "good" interview behaviors and "bad" interview behaviors may be determined. This same concept would also apply to trainee engagement behavior. The aspects of human behavior that the trainee excels or requires improvement may be determined by an oracle beforehand. Both general labels and feature specific labels may be implemented into the interview class vector. This can be understood as classifying the trainee's overall behavior during the interview, and also classifying aspects of the trainee's behavior for a qualitative performance review. These aspect labels may be linked to the trainee's associated extracted features (e.g., a nervous hand movement label may be linked to extracted hand key points).

Embodiments may be configured to classify interviews as "out-of-box," based on the model, dataset, and labelling. However, options may be provided for a user to apply their own personal labelling components of interviews based on experience or hindsight rather than using labels determined from prior expertise.

Embodiments provided herein may be configured to deal with a wide variety of audiovisual information. Inferences may be made from body key points, motion, image, and audio information. Algorithms for classifying human behavior generally focus on mapping images or audio information (such as image heat maps or audio recognition). Formatting can be applied to track key point data and audio cepstrum in a transfer learning scenario. Similarly, some embodiments are configured for classifying data based on changes between frames. A training element may be formatted to include information about two frames separated by a time interval to classify time varying behaviors. This formatted data may be flattened into a single training element. A specialized architecture implementation may be utilized for training elements that contain a combination of transferred data and frame data in order to robustly recognize feature performance (e.g., recognizing voice calmness, conversation speed, hand usage, and aspects of the eye motion from a single video test element). A Bayesian convolutional neural network architecture may be utilized to classify these spatially unique training and test elements. A development process may determine processes for pooling, optimization, acquisition, activation, and dropout to prevent issues with fitting.

Some embodiments are configured to train a model with one or more user owned confidential recordings based on user-specific metrics that may be more desirable than pre-trained models. This capability may be implemented through an active learning type architecture, user friendly interface, and acquisition function. The acquisition function may select one or more points from a pool of unlabeled data elements from the data set, with the pool points lying outside of the training set. The users may be prompted to label the selected elements as they desire (e.g., this was a bad interview because the conversational speed was too fast and voice was anxious). These selected elements may be added to existing training set, and a new model may be trained on the updated training set. This process may be repeated, with the training set increasing in size over time. Depending on the complexity and scale, server usage could be provided to further expedite this process.

Embodiments may also include a dialog assessment platform that combines the benefits associated with AI evaluation with audio feedback responses that are voiced by someone familiar with the learner. Such embodiments free up a tremendous amount of time and resources for evaluators while reducing the amount of inherent bias and human error typically associated with this type of assessment.

An extensive backend management platform is also included and allows for the bulk creation, distribution, and management of user accounts, all of which can be assigned to multiple levels of hierarchy within any given organization (e.g., administrator, teacher, research assistant, and student). With the addition of the proposed AI integration and the development of a simple editing console, members of a learning community may have access to platform features that are assigned by user type.

Diagnosing communication performance in a deep learning architecture may utilize extraction of key verbal and non-verbal features. Generally speaking, different algorithms excel at different aspects of human behavior. For example, an algorithm measuring body movements might efficiently track the arms, chest waist, legs, and feet at the cost of neglecting or poorly performing on the fingers, eyes, and facial features. Similar patterns apply with the analysis of vocal information (e.g., speech recognition, rate of speech, tonality, etc.) and with the detection of perceived emotions (e.g., empathy, surprise, anger, confusion, etc.). Similar patterns apply with the analysis of vocal information (e.g., speech recognition, rate of speech, or tonality) and with the detection of perceived emotions. Additionally, the detected behaviors will be rated against known standards, and report results that are aligned spatially to the video's timeline. Analytical results may be presented in a format that can assist with the production of feedback interventions that can take the form of human-voiced audio commentary.

Embodiments may be configured for inferring a trainee's patient communication skills, also known as "stacking." These embodiments may include facial tracking, body tracking, vocal tone detection and/or speech recognition. A classification scheme that includes benchmarks and deviated performance classes may be employed to detect emotions, measuring the frequency of each detection between given time marks. For body tracking, embodiments may analyze stance of a medical student under examination between similar time marks. Tonal analysis may rely on landmarks related to an empathetic tone. Natural language processing and linguistics may focus on determining sentiment and analyze conversational dialogue. The machine learning technologies capable of accomplishing these aims may be independently developed and/or pooled from frameworks such as MediaPipe™, OpenPose™, TensorFlow™, Natural Language Toolkit™, SciPy™, etc. Additionally, logic for conversation transcription and sentiment analysis, such as Azure's™ Speech and Cognitive Services may also be utilized.

Systematic "stacking" and "soft voting" utilize statistical data to make inferences based on relative significance regarding overall performance. Stacking may be used to help determine the best way to combine these predictions and soft voting will take into account the probability of the predicted class of the overall performance. The stacking meta-learner may be used to discover relational strengths and weaknesses between the base technologies (facial tracking, tonal analysis, etc.). Soft voting may be used to determine if there is a significant correlation between behavioral components. Individual statistical data may be examined for potential causation. Additional functions may be utilized to determine which points in the time frame the behavior originated. These established points may be utilized to inform an instructor as to potential areas within a video that may warrant intervention. For example, a trainee might have good vocal tone but need work in the usage of certain elements of body language such as eye contact. The segment of audio and video that has been analyzed for overall performance metrics may then be saved and marked in the video's timeline for further evaluation.

Accordingly, some embodiments may include a timeline feature that may be separated into two tracks. The top track will accommodate video files and the bottom track may be reserved for audio feedback files. Embodiments may also include a video compilation tool. Placement of multiple video files into the timeline may be performed by dragging-and-dropping individual files or by pre-selecting multiple files and adding them at the same time. Once placed in the timeline, the linear sequence of the video clips may be modified by selecting the individual clip and dragging the clip (and/or an icon/shortcut to the clip) to a new location in the timeline.

In addition to the AI assisted placement of pre-recorded audio files, evaluators can place audio feedback clips within the timeline through drag-and-drop processes of an audio insertion tool. If an appropriate pre-recorded file does not exist, the evaluator can use an audio recording tool with media buttons that include record, pause, and stop. The audio recording can take place during video playback or when video has been paused. Upon selecting "stop," the user can choose to "save" the file that embeds it in timeline, or select "save as," which will embed it in timeline and allows users to label the file and store it in their personal audio retrieval library.

The presence of an audio file within the timeline, regardless of how the file was inserted, may cause the playback volume levels for audio transmissions associated with the video file to be lowered; in some embodiments by approximately 70%. The inserted audio file may bring the volume of the two simultaneous sound tracks back up in some embodiments by approximately 100%. When the inserted audio file has no discernable sounds associated with it and/or when the inserted audio file is no longer playing, the volume level associated from the video will return to default levels.

Embodiments may include a play head feature. In these embodiments, the media console will contain a play head that can be scrubbed to any point on the timeline. As the play head is moved, a visual representation of the video may be displayed in real time.

Controls may be provided so that the rate at which a video is viewed can be accelerated or decelerated. Preset buttons (e.g., 0.75X, 1.0X, 1.25X, 1.5X, etc.) may be provided to the viewer. By default, any videos that are opened by the player may be set to playback at the default setting of 1.0X.

The console may present editing tools such as select, split, copy/paste, delete, etc. The overall intent of this feature is to allow users to quickly and easily remove content from a video compilation and/or add video clip at any specific point in the timeline.

It should be understood that deep fake software may also be utilized in some embodiments. As an example, if a student has recorded a video and the system has identified points of correction, these embodiments may also create a deep fake video of the student that corrects the points of correction. Stated another way, the deep fake video may include an artificially created video of the trainee performing as desired. The deep fake may also utilize overlays (such as a brightly colored circle, arrow, etc.) that highlight the desired points that were corrected in the deep fake video and/or points that need to be corrected in the original video. The systems and methods for providing a dialog assessment platform incorporating the same will be described in more detail, below.

Referring now to the drawings, FIG. 1 depicts a computing environment for providing a dialog assessment platform, according to embodiments described herein. As illustrated, the network environment may include a network 100, such as the internet, public switched telephone network, mobile telephone network, mobile data network, local network (wired or wireless), peer-to-peer connection, and/or other network for providing the functionality described herein.

Coupled to the network 100 are a trainee computing device 102a, a trainer computing device 102b, an administrator computing device 102c, and a remote computing device 104. Each of the computing devices 102, 104 may represent one or more different computing devices for providing the functionality provided herein and, as such, may be configured as a server, a personal computer, tablet, database, mobile device, and/or other computing device. As the trainee computing device 102a, the trainer computing device 102b, the administrator computing device 102c, and the remote computing device 104 may be utilized for capturing audio and/or video, one or more of these devices may include a camera (video and/or still image, natural light, infrared, heat sensing, etc.), microphone, speaker, and/or other similar hardware. The trainee computing device 102a may be any computing device that is used as a portal to access the dialog training platform. A trainee may communicate with a trainer interviewer to practice interviewing skills (or other tasks). Additionally, a browser extension or other application may be stored by the trainee computing device 102a for providing this functionality. As such, some embodiments may be configured such that at least a portion of this functionality may be provided locally by the trainee computing device 102a without a connection to the network 100.

Similarly, the trainer computing device 102b may include one or more computing devices for providing feedback to the trainee. The trainer computing device 102b may be operated by an instructor, who may help train one or more different trainees. In some embodiments, each trainer is assigned to a trainee, while in other embodiments trainees may work with a plurality of different trainers. As such, it will be understood that while a single trainee computing device 102a and a single trainer computing device 102b are depicted in FIG. 1, this is merely one example. Similarly, the administrator computing device 102c may also be provided for overseeing training provided by the instructors to the trainees.

The remote computing device 104 may be utilized to facilitate the communication among the trainee computing device 102a, the trainer computing device 102b, and the administrator computing device 102c. Specifically, some embodiments may be configured to store video, provide artificial intelligence video processing, provide a communication portal, and/or provide other functionality described herein. To this end, the remote computing device 104 may include a memory component 140, which may store content logic 144a and feedback logic 144b. The content logic 144a may be configured to cause the remote computing device 104 to manipulate content captured related to a dialog, including storage, analyzing, etc. Similarly, the feedback logic 144b may be configured to cause the remote computing device 104 to facilitate the providing of feedback, whether the feedback come from the remote computing device 104, as described in more detail below.

Figure 2:
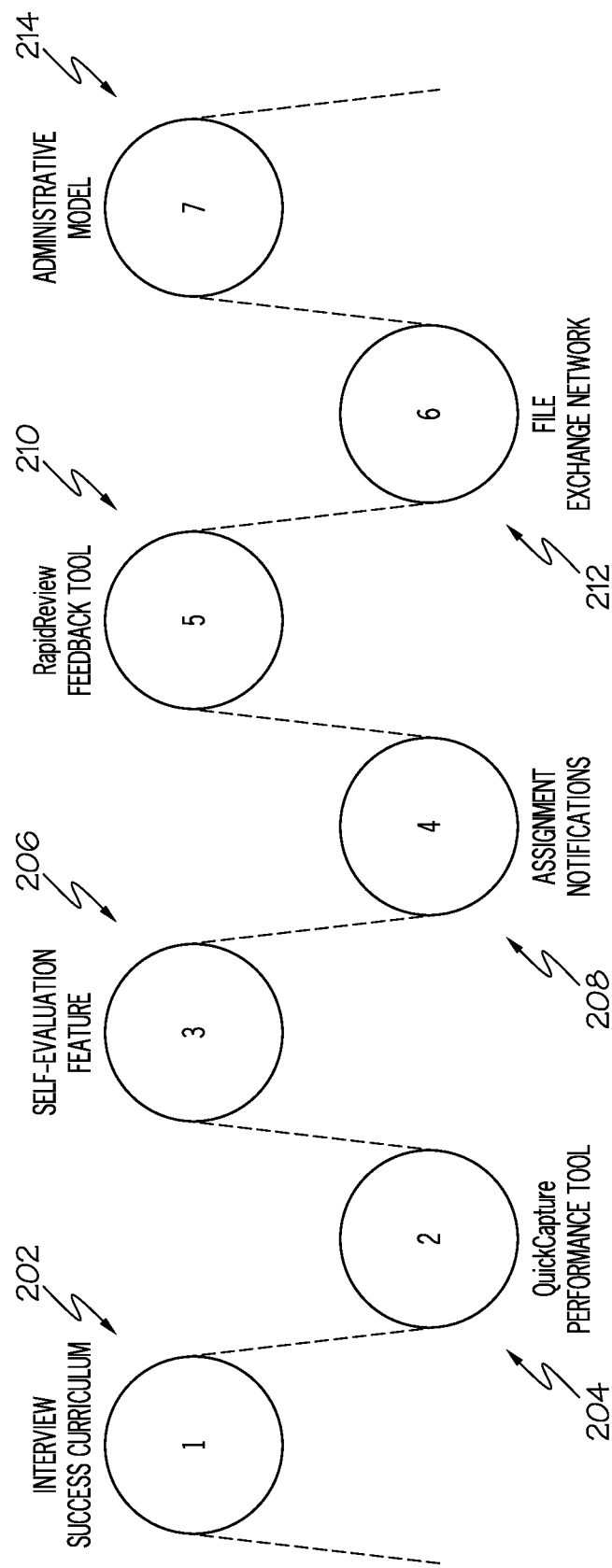
FIG. 2 depicts a workflow diagram for providing a dialog assessment platform, according to embodiments described herein.

FIG. 2 depicts a workflow diagram for providing a dialog assessment platform, according to embodiments described herein. As illustrated, an interview success curriculum component 202 may be utilized to create and provide a training curriculum for a trainee. A quick capture performance tool component 204 may be utilized to facilitate and/or provide a platform for conducting, recording, and storing an interview of a trainee. A self-evaluation feature component 206 may be utilized to provide a platform for a trainee to self-evaluate training sessions, such as a mock interview. An assignment notifications component 208 may be utilized to determine deadlines for assignments and provide a trainee, a trainer, and/or an administrator with notifications regarding the same. A rapid review feedback tool component 210 may be utilized for evaluating a trainee's training session, such as a mock interview. A file exchange network component 212 may be utilized for storage of video content, audio content, image content, as well as performance data, metadata, and/or other data. An administrative module component 214 may be utilized for an administrator to view, edit, and/or create functionality such as depicted in components 202-212.

FIG. 3 depicts a trainee user interface 330, according to embodiments provided herein. As illustrated, the trainee user interface 330 may be provided to a trainee and may include a screen capture option 332 and a webcam option 334. In response to selection of the screen capture option 332, an image of one or more user interfaces may be captured. Specifically, a recording of one or more screens, tabs, and/or applications on the subject computing device may be started. In response to selection of the webcam option 334, an attached webcam may be may be activated and the trainee may be connected with a trainer or other user.

FIG. 4 depicts another trainee user interface 430, according to embodiments provided herein. Once a recording selection is made in the trainee user interface 330 from FIG. 3, a share option 432 may be provided. In response to selection of the share option 432, the recording process may begin and pause and stop options may be provided.

After a recording is stopped, the resulting video may be played back. In some embodiments, playback may occur in a separate window almost immediately. Trainees can discard a video at any point after recording has stopped. There is a built-in delay before a trainee can select options to save their video. This is designed to encourage the trainee to review their efforts and improve upon them by recording another video if necessary.

By default, file name is set to the first and last name of user, followed by a timestamp (ex. Jane_Doe_18-May-2021_16-32). Although file name can be changed by the user. By default, video file saves to the last file location selected by the user. Referring back to FIG. 3, in response to selection of the webcam option 334, the webcam user interface 530 of FIG. 5 may be provided.

FIG. 5 depicts a webcam user interface 530 for a trainee, according to embodiments provided herein. In response to selection of the webcam option 334 from FIG. 3, a screen capture of at least a portion of the current display may be captured. As illustrated, the webcam user interface 530 includes a webcam option 532 and a picture-in-picture option 534. In response to selection of the webcam option 532, an onboard camera or attached webcam may be activated. Additionally, a camera window appears on screen and can be dragged to any location. In response to selection of the picture-in-picture option 534, a smaller onboard camera window may be launched and a camera window appears on screen, which can be dragged to any location. A record option, a pause option, and a stop option may be provided for controlling the recording.

FIG. 6 depicts a trainer user interface 630, according to embodiments provided herein. As illustrated, the trainer user interface 630 is configured for a trainer and/or evaluator and includes a feature set that includes a content video option 632, a webcam option 634, and a feedback option 636. In response to selection of the content video option 632, a screen capture and/or video capture may be performed, as described above. In response to selection of the feedback option 636, may provide access to a select video option. The resulting window may be provided for searching and retrieving video files. Retrieved video files appear in playback window. Playback controls include play, pause, and a timeline that can be scrubbed to any point in the video. When record is selected, a second audio track captures the voice of the person providing feedback. Feedback audio is dubbed into original video. The volume of original audio is reduced to approximately 30% with feedback audio taking approximately 70% of the volume. When no feedback audio is detected, the original volume returns to its default level (100%). In response to selection of the webcam option 634, the webcam may be launched, as described above.

FIG. 7 depicts a recording user interface 730 for a trainee, according to embodiments provided herein. In response to selection of the share option 432 from FIG. 4 (or a trainer if the webcam option 634 is selected from FIG. 6), the recording user interface 730 may be provided. The recording user interface 730 includes a record option 732, a pause option 734, and a stop option 736.

Figure 8:
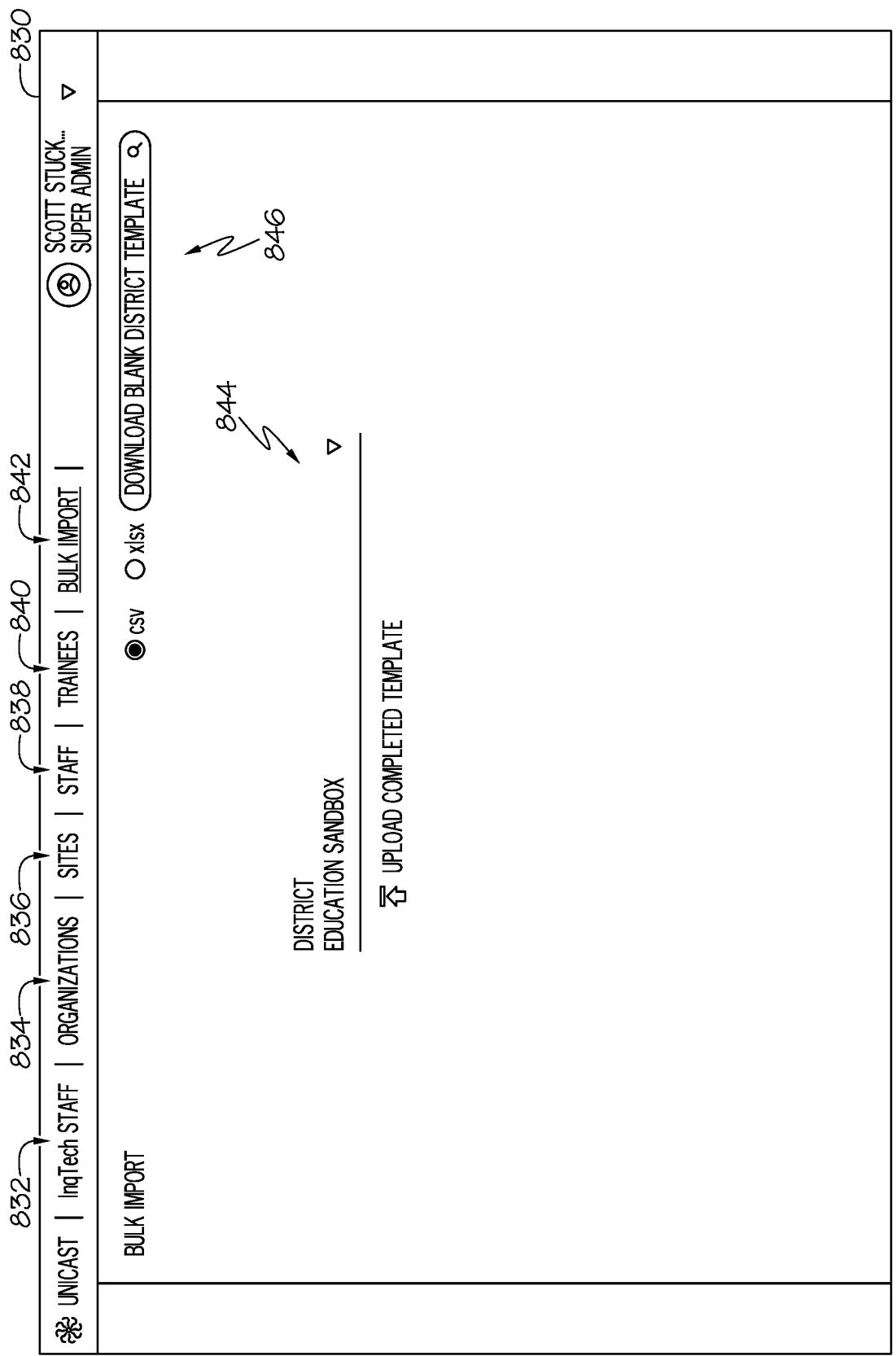
FIG. 8 depicts a bulk import user interface, according to embodiments provided herein.

FIG. 8 depicts a bulk import user interface 830, according to embodiments provided herein. As illustrated, the bulk import user interface 830 may include a staff option 832, an organizations option 834, a sites option 836, a staff option 838, a trainees option 840, and a bulk import option 842. As illustrated, the bulk import option 842 is selected. Also included is a district option 844 and a template option 846, which allow the user to download spreadsheets that are specific to an organization. These spreadsheets can be used to import potential users in bulk fashion into the system. Once these spreadsheets are completed, they can be uploaded to the system through the district option 844. Specifically, this feature may be restricted to site administrator level personnel and above. This allows for batch creation for an unlimited number of user accounts per site and can also be used to update or modify existing accounts at the site level.

Figure 9:
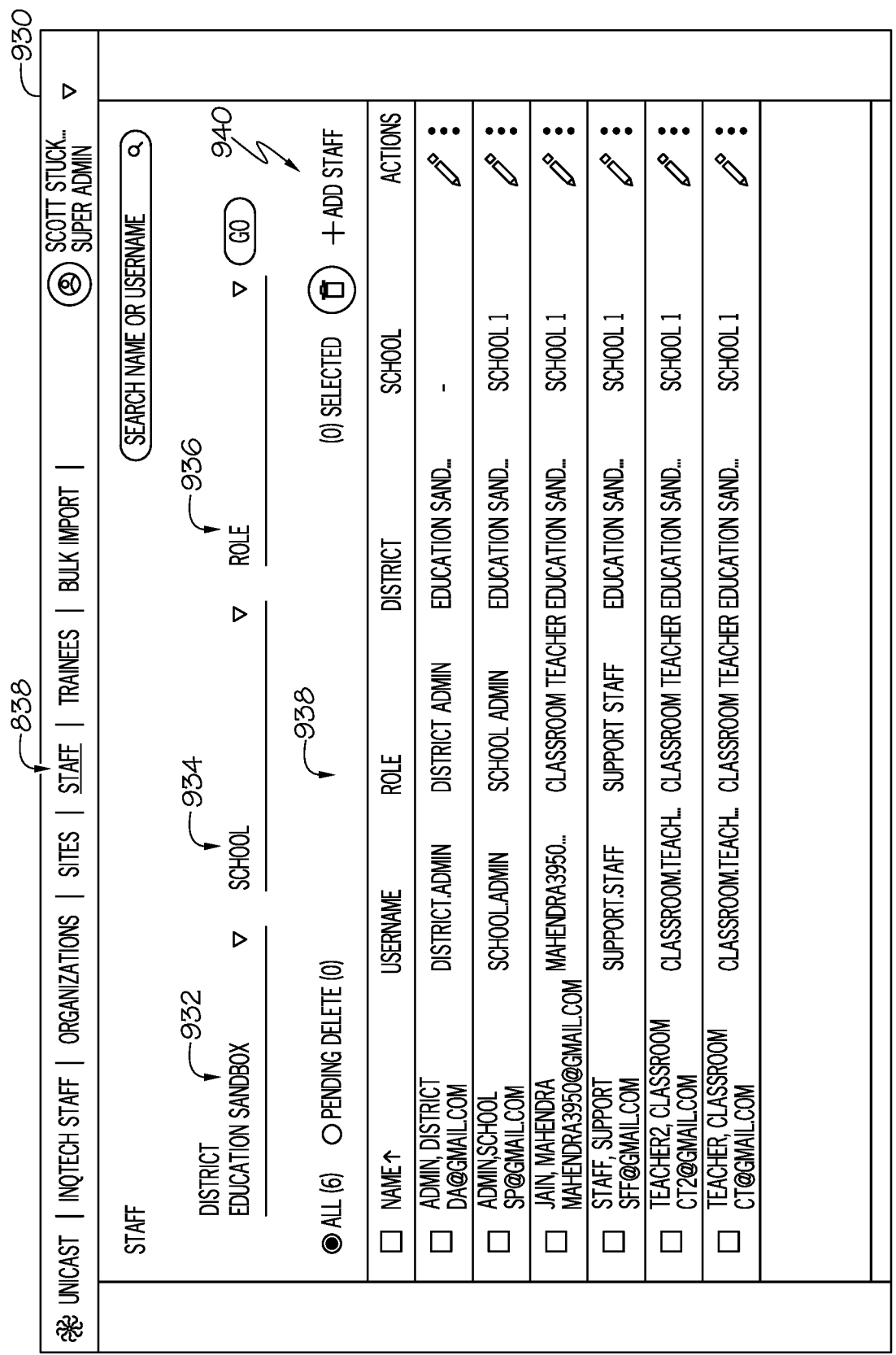
FIG. 9 depicts an administrative staff user interface, according to embodiments provided herein.

FIG. 9 depicts administrative interface 930 that displays information pertaining to staff members, according to embodiments provided herein. As illustrated, in response to selection of the staff option 838 (from FIG. 8 or other interfaces provided herein), the administrative interface 930 may be provided. Users can be assigned various roles at time of account creation and those roles can be modified at any time. As such, administrative users add additional staff and base user accounts as needed. The administrative interface 930 includes a district option 932 for selecting a desired district or organization, a school option 934 for selecting a desired school or site, and a role option 936 for selecting a desired role. A super admin also has the ability to add, edit, or delete organizations, their sites, staff members, and trainees. Also provided is a role section 938 that includes name, username, role, district, school, and action columns. The role section 938 may provide different information depending on the role of the user. For example, a district administrator can access and edit information contained within each school or site assigned to that organization. A user with the role of classroom teacher can only access student or trainee information associated with a particular site. An add staff option 940 is also provided for adding individual staff members to this listing or other listings.

Figure 10:
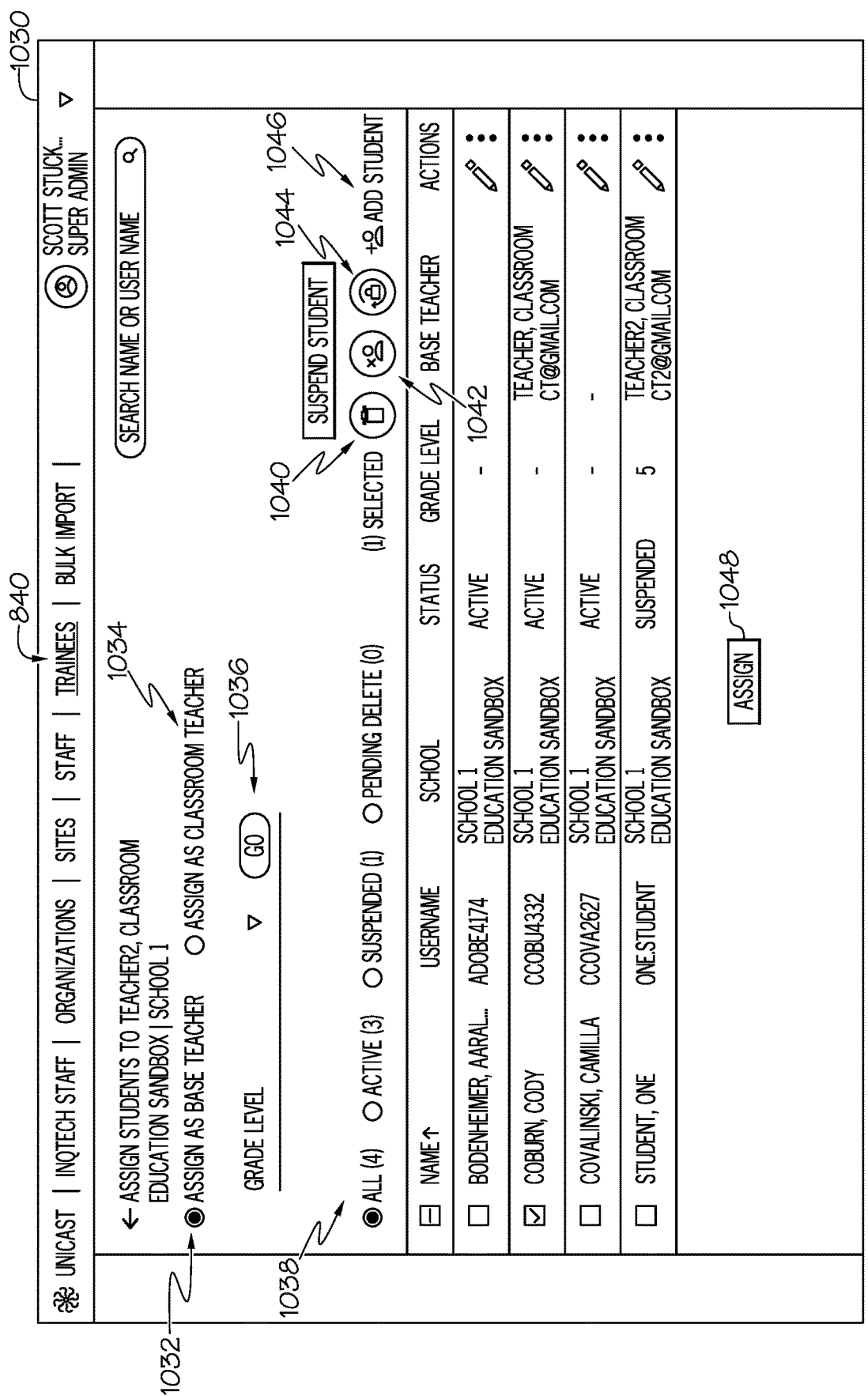
FIG. 10 depicts a trainers user interface, according to embodiments provided herein.

FIG. 10 depicts another administrator user interface 1030 that provides access to student/trainee information, according to embodiments provided herein. In response to selection of the trainees option 840 in FIG. 8 (or other interface), the administrator user interface 1030 may be provided. Specifically, the administrator user interface 1030 includes an assign as base teacher option 1032 and an assign as classroom teacher option 1034. In response to selection of the assign as base teacher option 1032, the selected teacher will be assigned as a "base teacher." In response to selection of the assign as classroom teacher 1034, the selected teacher will be assigned as a "classroom teacher." A grade level option 1036 is also provided for selecting the grade level for which the administrator user interface 1030 is assigning. A student/trainee list section 1038 is provided, which provides a list of students/trainees and the name of their associated supervisor (a base teacher or a classroom teacher). The student/trainee list section 1038 includes columns for a plurality of trainees, including name, username, school, status, grade level, base teacher designation, and actions. Also provided are a delete option 1040, a suspend option 1042, a reset password option 1044, and an add student option 1046. An assign option 1048 is also provided for confirming the selections made in the administrator user interface 1030.

Figure 11:
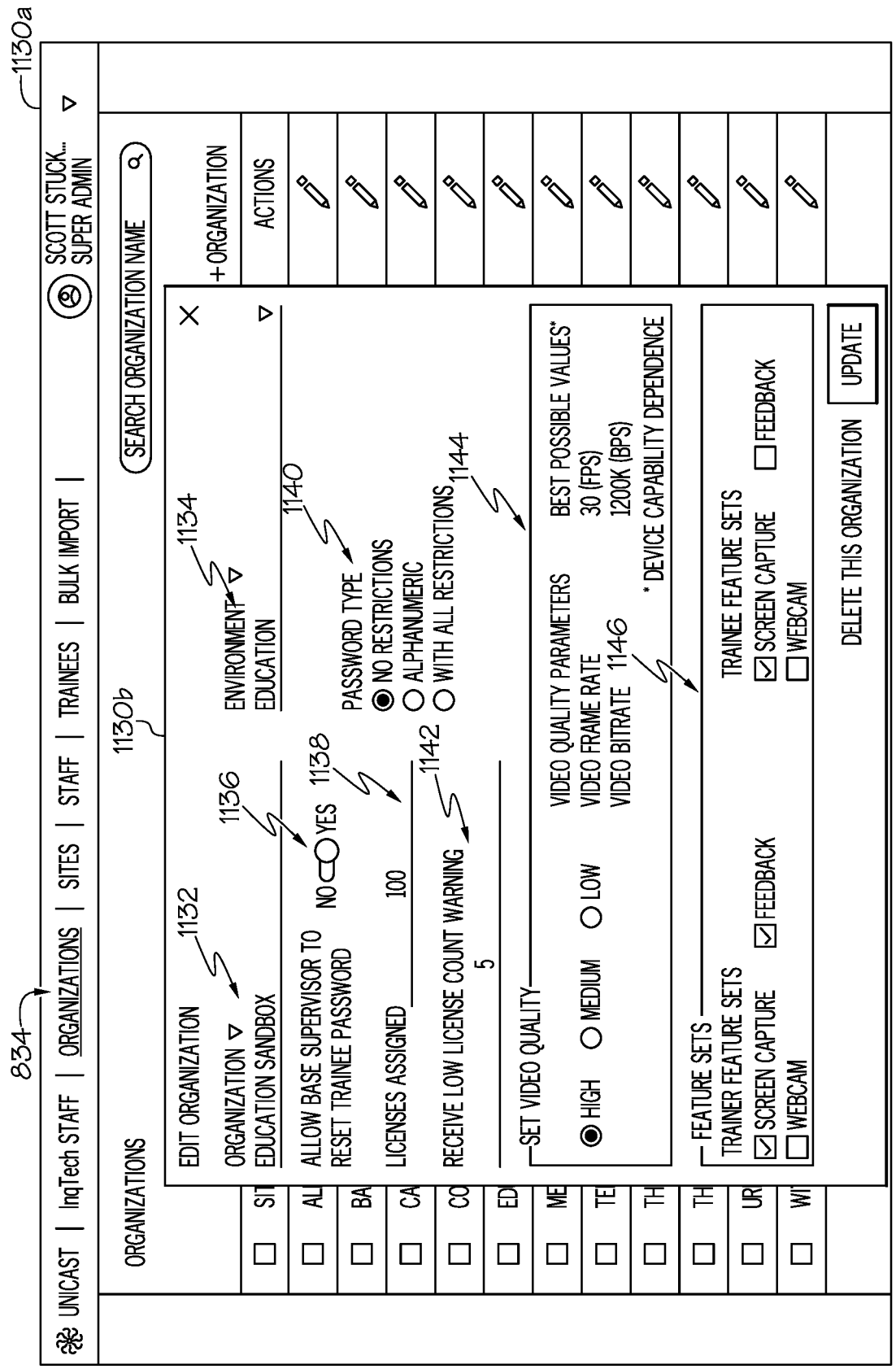
FIG. 11 depicts an edit organization user interface, according to embodiments provided herein.

FIG. 11 depicts an edit organizations user interface 1130b, according to embodiments provided herein. In response to selection of the organizations option 834 from FIG. 8 or other interface, an organization user interface 1130a may be provided. The organization user interface 1130*a* may provide a listing of organizations. In response to selection of an organization in the organization user interface 1130*a*, the edit organizations user interface 1130*b* may be provided. The edit organizations user interface 1130*b* provides an organization option 1132, an environment option 1134 (education or workforce), a trainee password option 1136, a licenses assigned option 1138, a password type option 1140, a low license count warning option 1142, a video quality option 1144, and a feature sets option 1146. The feature sets option 1146 includes options for setting screen capture, feedback, webcam for trainer and trainee feature sets.

Figure 12:
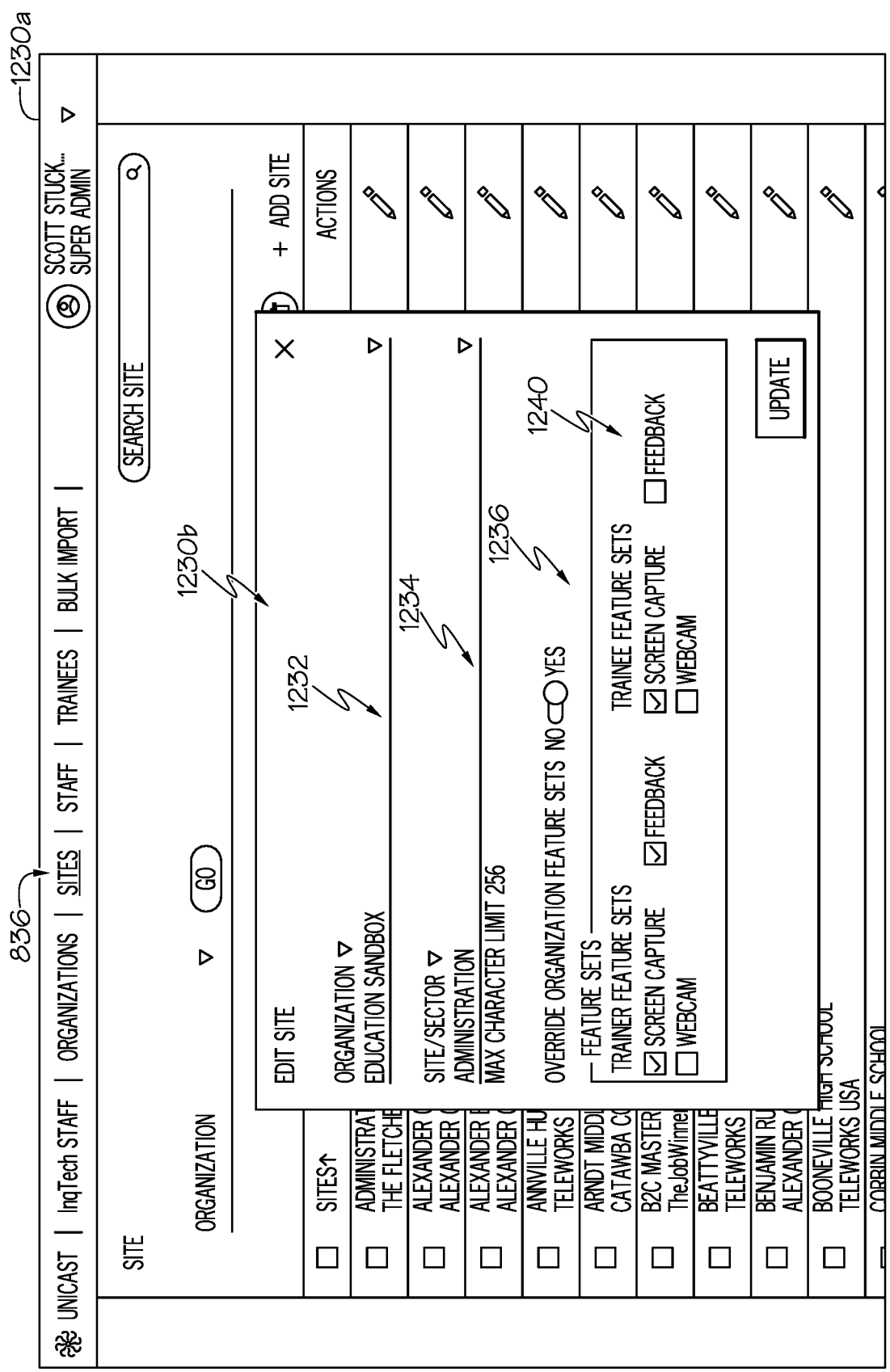
FIG. 12 depicts an edit site user interface, according to embodiments provided herein.

FIG. 12 depicts an edit site user interface 1230*b*, according to embodiments provided herein. In response to selection of the sites option 836 from FIG. 8 or other interface, a sites user interface 1230*a* may be provided. The sites user interface 1230*a* may include a listing of sites (in the example of FIG. 12, the sites are schools), as well as details on the listed sites. The edit site user interface 1230*b* may be provided to edit one or more of the sites and may include an organization option 1232, a site option 1234, an override organization feature sets option 1236, and a feature sets option 1240. The feature sets option 1240 may include options for screen capture, feedback, and webcam for trainer feature sets and trainee feature sets.

Figure 13:
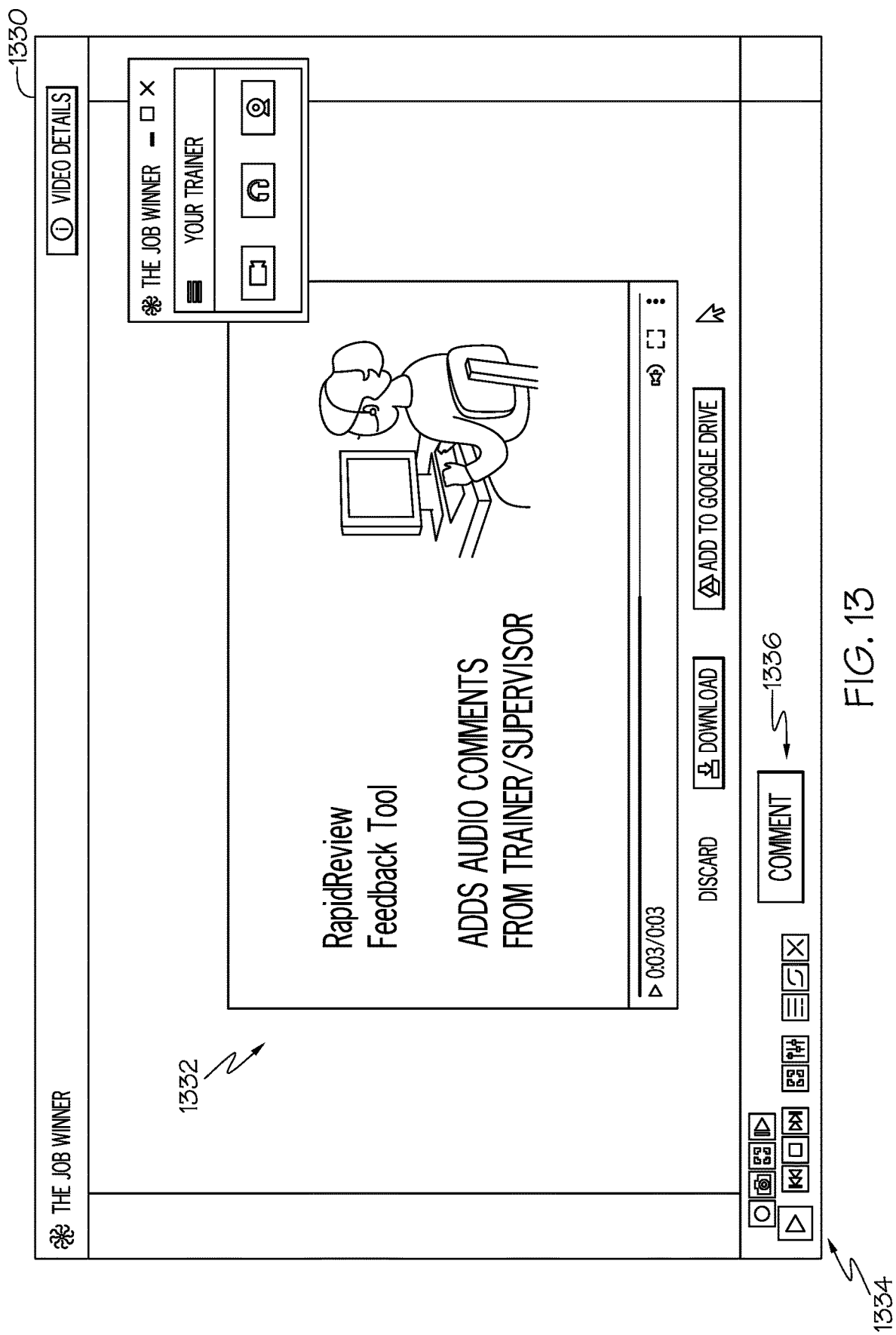
FIG. 13 depicts a trainer review user interface, according to embodiments provided herein.

FIG. 13 depicts a trainer review user interface 1330, according to embodiments provided herein. As illustrated, the trainer review user interface 1330 may include a video playback section 1332, control options 1334, and a comment option 1336. As described above, a trainee may engage in an interview or other training exercise. The interview may be with a live person and/or with a simulation, depending on the particular embodiment. Regardless, the mock interview may be virtual through the platform described herein and may be recorded using the options described above. Once the mock interview is complete, the trainer may review that interview via the trainer review user interface 1330. Specifically, the trainer review user interface 1330 may provide the video playback section 1332 for viewing the recorded video of the interview. Additionally, the control options 1334 may be provided, including play, rewind, pause, fast forward, etc. The comment option 1336 may also be provided and may allow the trainer to insert a prerecorded comment into the interview video or record a new comment that can be embedded into the interview video.

Specifically, as the trainer is reviewing the interview, he/she might notice a point of instruction. The trainer may select the comment option 1336, which will start recoding audio and/or video of the trainer making the comment. The comment will be overlaid on the interview video, so when reviewing, the trainee can hear both the original interview and the comment. If video is inserted, the trainer video may be a picture-in-picture structure to again see both the trainer and the interview.

Similarly, some embodiments may predict comments that the trainer may make, based on video and/or audio cues in the interview. Specifically, if the word "um" typically triggers the trainer to insert a comment, such as "please no filler words," the trainer review user interface 1330 may provide a notification to the trainer. The trainer may also be presented with an option to insert a previously recorded comment in the spot where the trainee said the word "um". Similarly, embodiments may track eye contact of the trainee in the video and provide the trainer with information regarding the time with eye contact and the time without eye contact for the trainer to comment. It should be noted that, while in some embodiments this may include simply viewing the camera directly, some embodiments may calculate the position of the interviewer on the trainee's monitor, as well as the position of the webcam. These embodiments may then calculate the angle of the webcam and the angle of the image to approximate eye contact.

Some embodiments may be configured to compile the comments and create a deep fake video of the trainee that shows him/her in a proper interview, based on the trainer's comments. As an example, the deep fake video may remove filler words; may provide the appropriate eye contact; may include the proper posture; etc. Thus, when the trainee views the comments, he/she can also view the quality difference in the deep fake and their own interview.

Figure 14:
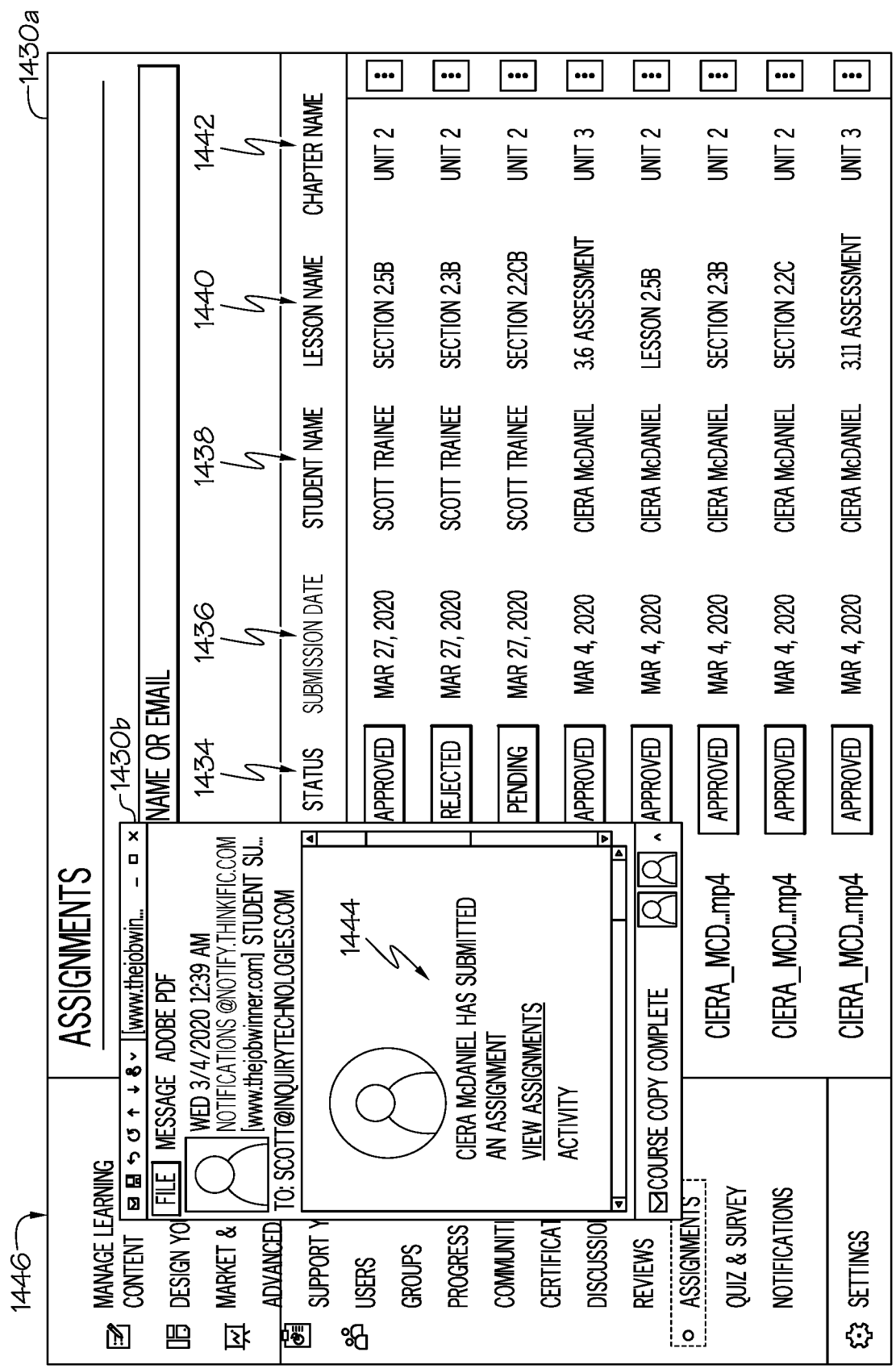
FIG. 14 depicts an assignment user interface, according to embodiments provided herein.

FIG. 14 depicts an assignment user interface 1430*a*, according to embodiments provided herein. As illustrated, the assignment user interface 1430*a* includes a video column 1432 that lists each video associated with an assignment. Column 1434 provides the status of the assignment. Column 1436 provides a submission date for the assignment. Column 1438 provides the student (or trainee) who submitted the video and/or was tasked with the assignment. Column 1440 provides the lesson name associated with that video. Column 1442 provides the chapter name.

In response to a student submitting a new assignment, a user interface 1430*b* may be provided as a notification. The user interface 1430*b* may provide a data section that provides the student's name, the activity, the video name, and/or other information associated with that submission. Also provided in the assignment user interface 1430*a* is a sidebar 1446. The sidebar 1446 may provide a plurality of other options, as provided in FIG. 14.

Figure 15:
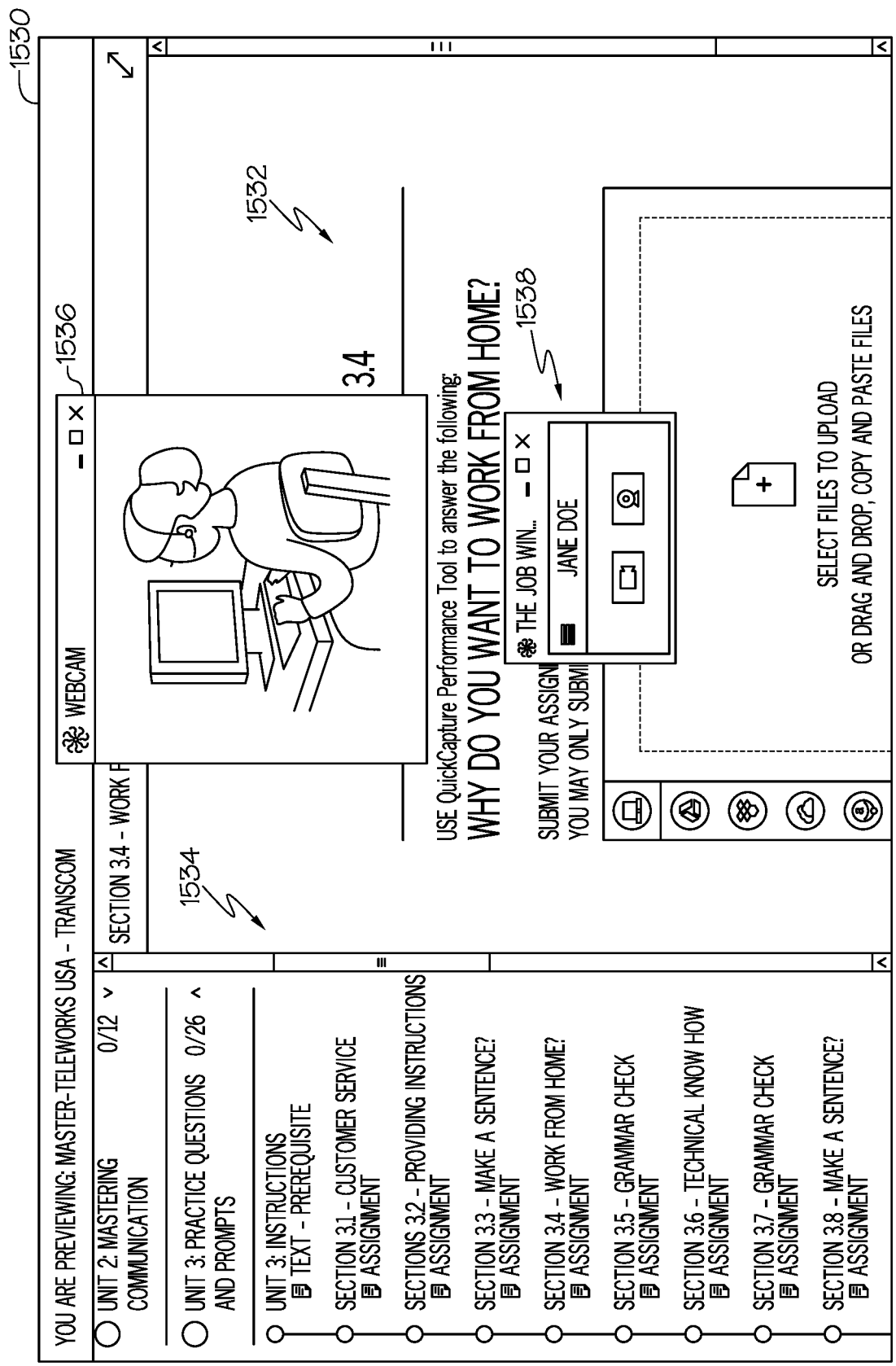
FIG. 15 depicts another assignment user interface, according to embodiments provided herein.

FIG. 15 depicts an assignment user interface 1530, according to embodiments provided herein. As illustrated, the assignment user interface 1530 includes a content section 1532 and a sidebar section 1534. The sidebar section 1534 may provide a plurality of options that a trainee may select for completing an assignment, practicing a task, and/or otherwise training. As illustrated, "unit 3" in the sidebar section 1534 includes practice questions and prompts. Also provided in the sidebar section 1534 are instructions and assignments associated with "unit 3," such as customer service, providing instructions, make a sentence, work from home, grammar check, technical knowhow, etc.

In response to selection of one of the assignments in the sidebar section 1534, the content section 1532 may update. As illustrated, this may include customizing the content, including files provided. Updating may also include a video window 1536 and control window 1538. The video window 1536 and the control window 1538 may be utilized to conduct a video training session and record that video training session, as described above.

Figure 16:
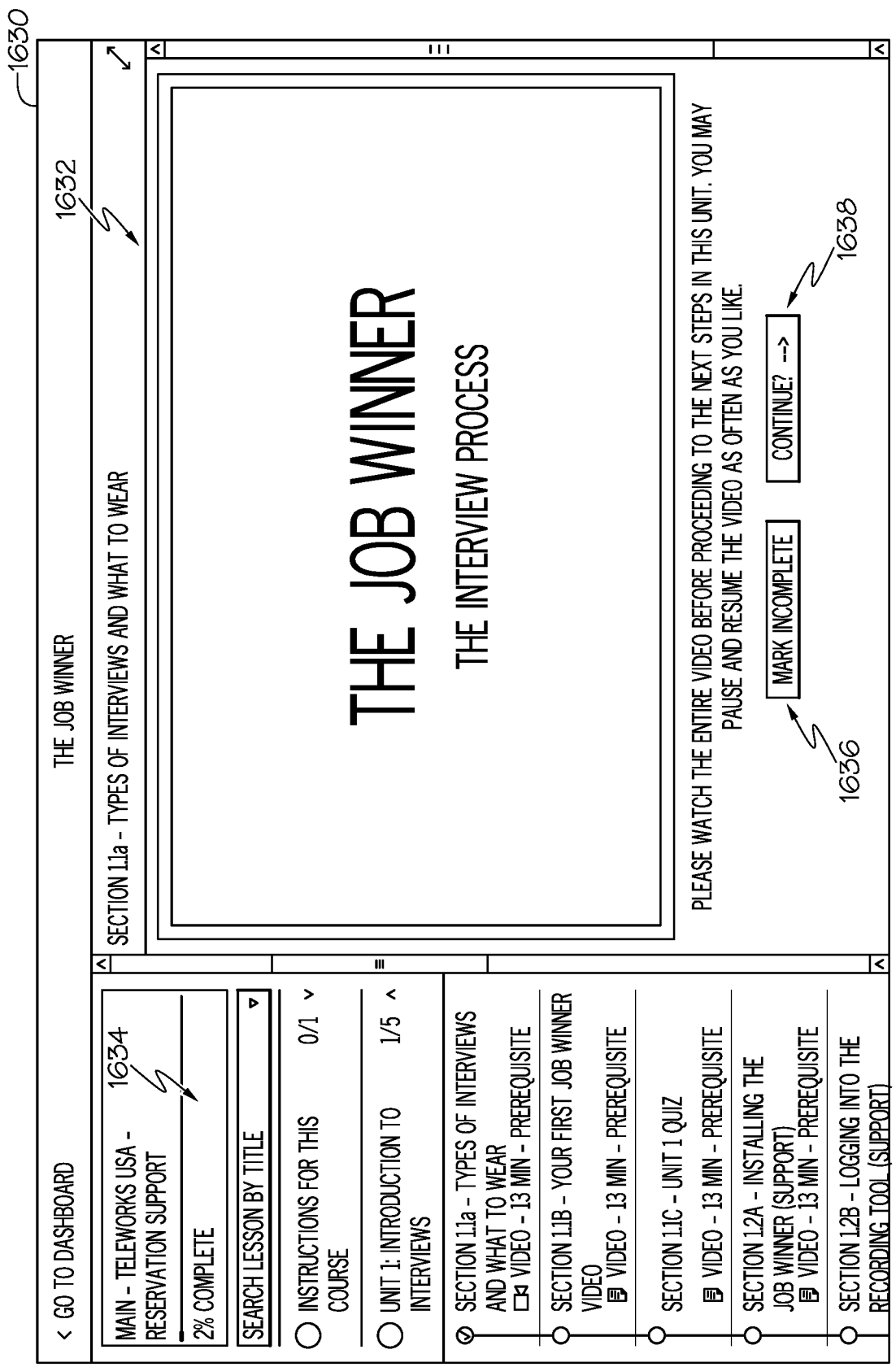
FIG. 16 depicts a content user interface, according to embodiments provided herein.

FIG. 16 depicts a content user interface 1630, according to embodiments provided herein. As illustrated, the content user interface 1630 provides a content section 1632 and a sidebar section 1634. The content section 1632 may provide information selected from the sidebar section 1634 and may include a video for the trainee to watch. A mark incomplete option 1636 and a continue option 1638 may be selected to re-watch or continue to the next segment.

Figure 17B:
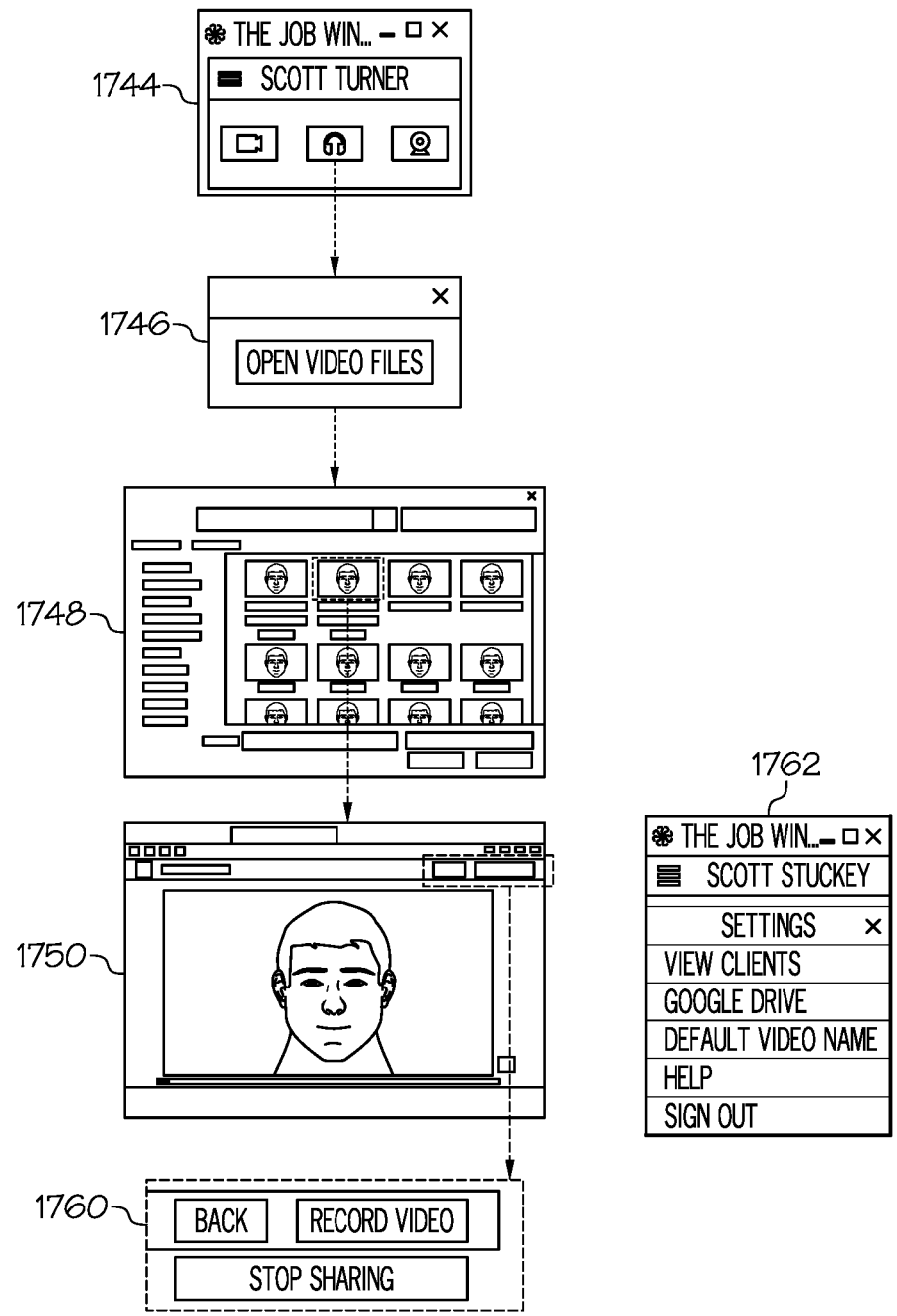

FIGS. 17A-17B depict a plurality of user interfaces for providing a dialog assessment platform, according to embodiments described herein. As illustrated in block 1730, a user interface may be provided with a record option and a webcam option. In response to selection of the webcam option, in block 1732 options may be provided for opening a webcam and/or activating picture-in-picture. In block 1734, in response to selection of the webcam option, recording options (record, pause, and stop) may be provided to record images from the webcam.

In block 1736, in response to selection of the picture-in-picture option the entire screen may be recorded, including live webcam inset. In block 1738, in response to recording starting from block 1736 or selection of the create a content video option from block 1730, screen recording options may be provided, including recording the entire screen, recording a particular browser tab/window, and/or recording any application window. In block 1740, once the selection is made, a share option may be provided to start recording. In block 1742, pause and stop options may be provided to interrupt recording.

As illustrated in FIG. 17A, embodiments described herein may be configured to provide one or more options for recording a dialog. In some embodiments, the dialog may be a training session for an interview, where the trainee is training for job interviews. In these embodiments, the trainee may initiate recording of the training session. The training session may be a mock interview with a human and may be conducted via video conference technologies (e.g., using the administrator computing device 102c and/or in person, with the trainee computing device 102a recording the discussion). In some embodiments, the training session may include recorded or simulated interview questions provided to the trainee, which can be replayed at the discretion of the trainee.

Regardless, the trainee may receive the interview questions and provide answers while the trainee computing device 102a is recording. Upon completion, the trainee computing device 102a may require the trainee to review the recorded interview and/or provide one or more user interfaces for the trainee to self-evaluate his/her responses. Upon reviewing and/or otherwise completing the training, the recording data may be communicated to the instructor. The instructor may be provided with one or more user interfaces for evaluating the dialog and providing feedback for the trainee. As an example, the user interfaces may include a user interface for the instructor to capture audio (and/or video) template comments. In this example, the instructor may record comments that the instructor often uses. Thus, when evaluating a dialog, the instructor may drag and drop or otherwise insert the template comment at the desired point in the recording. Similarly, some embodiments may be configured to automatically determine commonly used comments for an instructor and automatically create the template comment for future use.

Some embodiments may be configured for the instructor to insert the template comment and/or unique comments that are recorded on top of the audio provided by the trainee, such that the trainee may review the comments while viewing and listening to his/her recording. Accordingly, the trainee may review the recording and comments in real time, increase the speed, and/or decrease the speed, and the comments will be adjusted accordingly.

Some embodiments may also use artificial intelligence to screen the recording and flag points that the instructor will likely wish to provide comments. As an example, embodiments may be configured to identify filler words used by the trainee and flag those portions of the recording for the instructor to specifically review and provide comments.

FIG. 17B provides block 1744, which depicts a trainer default interface. The trainer default interface includes a create content video option, a create feedback video option, and a webcam option. Block 1746 provides a search criteria interface for opening video files. Block 1748 includes a listing of video options and block 1750 includes a user interface providing one or more of those videos, with a record video option provided. Block 1760 indicates that selection of the record video option provides audio feedback recording. Audio recording stops when a stop sharing option is selected. Block 1762 provides a plurality of menu options.

As illustrated, the interfaces provided in FIGS. 17A, 17B represent the instructor's feedback experience. These features include an option to search for video files only, audio from instructor recorded over any audio present in trainee's video (example of volume levels—70% instructor/30% trainee). An option may also be provided for saving audio feedback file before inserting the feedback in trainee's video.

Figure 18:
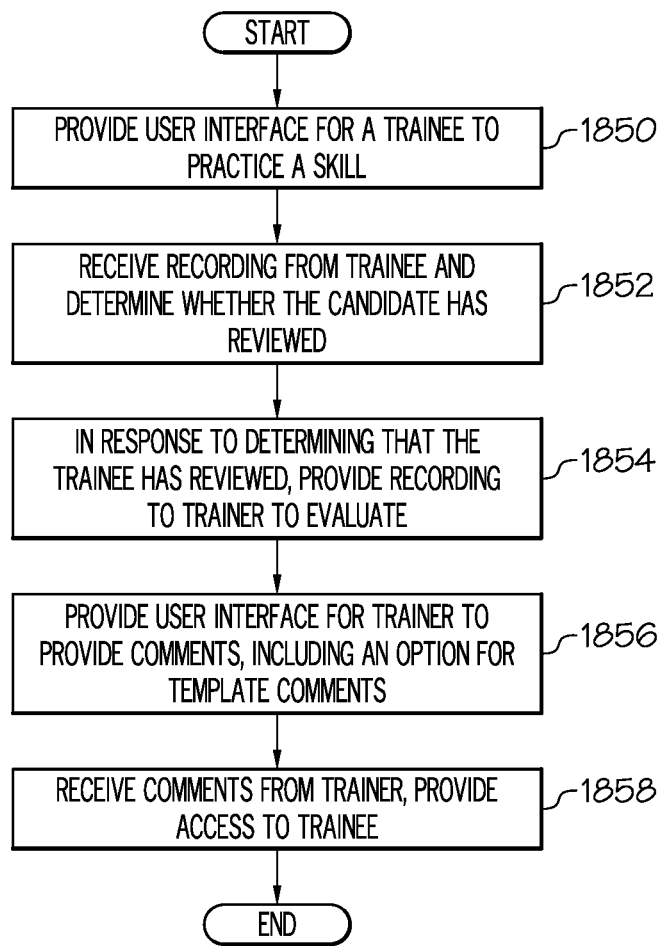
FIG. 18 depicts a flowchart for providing a dialog assessment platform, according to embodiments described herein.

FIG. 18 depicts a flowchart for providing a dialog assessment platform, according to embodiments described herein. As illustrated in block 1850, a user interface may be provided for a trainee to practice a skill. In block 1852, a recording may be received from the trainee and a determination may be made regarding whether the trainee has reviewed the recording. In block 1854, in response to determining that the trainee has reviewed, the recording may be provided to the instructor to evaluate. In block 1856, a user interface may be provided for the instructor to provide comments, including an option for template comments. In block 1858, the comments may be received from the instructor and access may be provided to the trainee.

Figure 19:
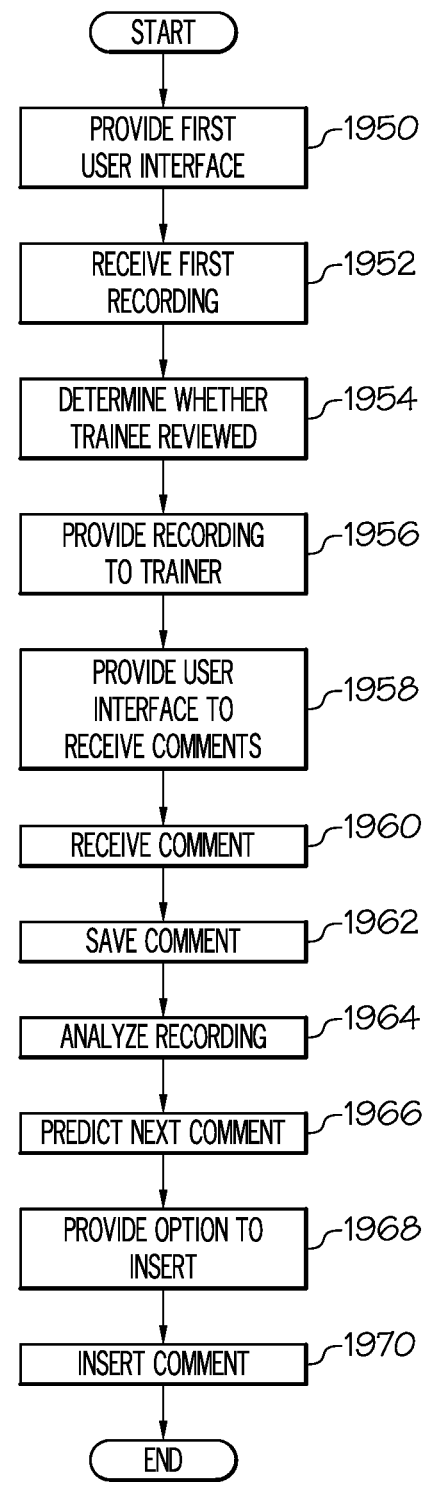
FIG. 19 depicts a flowchart for providing skill assessment training, according to embodiments provided herein.

FIG. 19 depicts a flowchart for providing skill assessment training, according to embodiments provided herein. As illustrated in block 1950, a first user interface for a trainee to practice a skill may be provided, where the first user interface provides an interaction with the trainee. In block 1952, a first recording from the trainee practicing the skill may be received. In block 1954, a determination may be made regarding whether the trainee has reviewed the first recording.

In response to determining that the trainee has reviewed the first recording, blocks 1956-1968 may be performed. Specifically, in block 1956, the first recording may be provided to a trainer. In block 1958, a second user interface may be provided for the trainer to provide comments to the first recording. In block 1960, a comment may be received from the trainer at a first section of the first recording. In block 1962, the comment may be saved as a previously recorded comment. In block 1964, an analysis of the first recording may be performed to determine a feature of the interaction that corresponds to the previously recorded comment. In block 1966, a prediction may be made when the trainer will provide the previously recorded comment to a second section of the recording, based on the analysis of the feature. In block 1968, an option may be provided to the trainer to insert the previously recorded comment into at the second section. In block 1970, in response to selection of the option, the previously recorded comment may be inserted at the second section.

Figure 20:
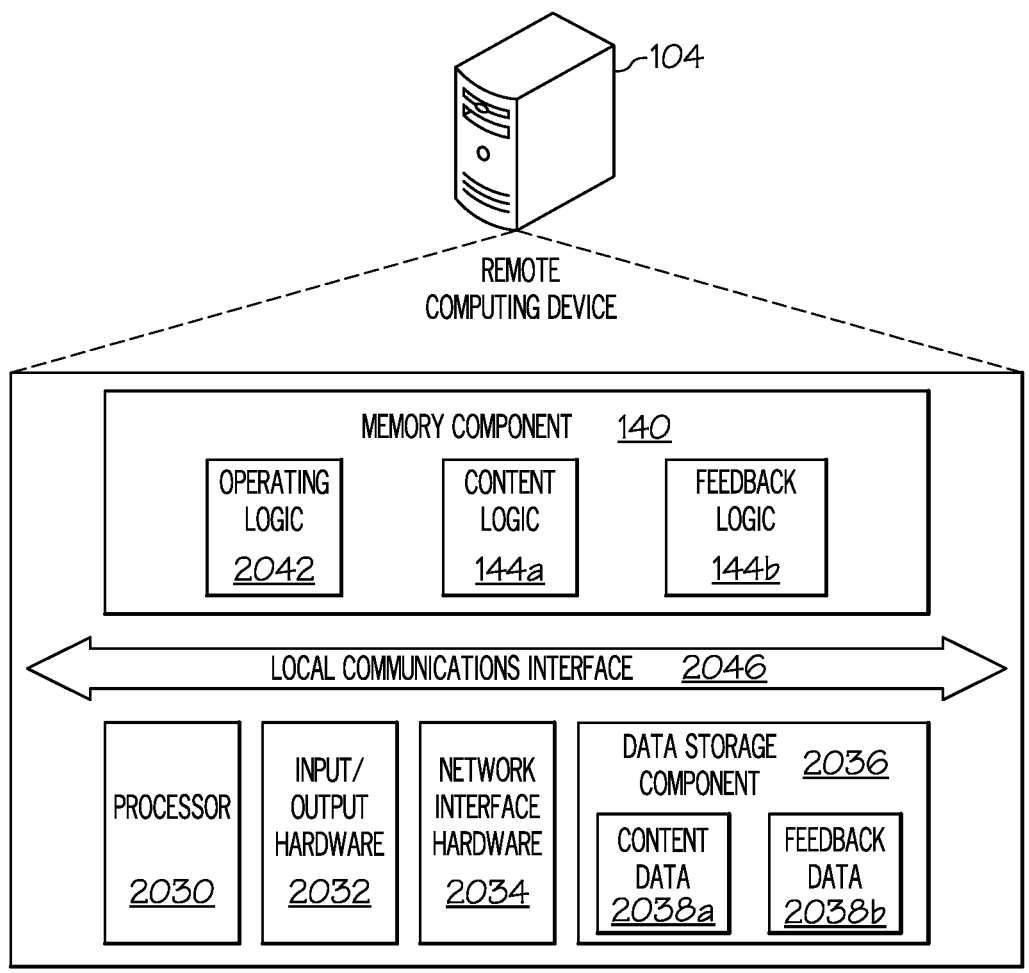
FIG. 20 depicts a computing device for providing a dialog assessment platform, according to embodiments described herein.

FIG. 20 depicts a remote computing device 104 for providing a dialog assessment platform, according to embodiments described herein. As illustrated, the remote computing device 104 includes a processor 2030, input/output hardware 2032 (which may include and/or be coupled to a webcam, keyboard, mouse, monitor, and/or other input/output device), network interface hardware 2034, a data storage component 2036 (which stores content data 2038a, video data 2038b, and/or other data), and the memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the remote computing device 104 and/or external to the remote computing device 104.

The memory component 140 may store operating system logic 2042, the content logic 144a, and the feedback logic 144b. The content logic 144a and the feedback logic 144b may each include a plurality of different pieces of logic, each of which may be embodied as a computer program or module, firmware, and/or hardware, as an example. A local interface 2046 is also included in FIG. 20 and may be implemented as a bus or other communication interface to facilitate communication among the components of the remote computing device 104.

The processor 2030 may include any processing component operable to receive and execute instructions (such as from a data storage component 2036 and/or the memory component 140). As described above, the input/output hardware 2032 may include and/or be configured to interface with a microphone, camera, speaker, and/or the components of FIG. 20.

The network interface hardware 2034 may include and/or be configured for communicating with any wired or wireless networking hardware, including an antenna, a modem, a LAN port, wireless fidelity (Wi-Fi) card, WiMAX card, mobile communications hardware, and/or other hardware for communicating with other networks and/or devices. From this connection, communication may be facilitated between the remote computing device 104 and other computing devices, such as those depicted in FIG. 1.

The operating system logic 2042 may include an operating system and/or other software for managing components of the remote computing device 104. As discussed above, the content logic 144a may reside in the memory component 140 and may be configured to cause the processor 2030 to capture, store, and manipulate content, as described above. Similarly, the feedback logic 144b may be utilized to assist the instructor in providing feedback to the trainee, and/or providing other similar functionality.

It should be understood that while the components in FIG. 20 are illustrated as residing within the remote computing device 104, this is merely an example. In some embodiments, one or more of the components may reside external to the remote computing device 104. It should also be understood that, while the remote computing device 104 is illustrated as a single device, this is also merely an example. In some embodiments, the content logic 144a and the feedback logic 144b may reside on different computing devices. As another example, one or more of these functionalities and/or components may be provided by a remote computing device 104, the trainee computing device 102a, the trainer computing device 102b, the administrator computing device 102c, and/or other devices, which may be coupled to the remote computing device 104 via the network. These devices may also include hardware and/or software for performing the functionality described herein.

Additionally, while the remote computing device 104 is illustrated with the content logic 144a and the feedback logic 144b as separate logical components, this is also merely an example. In some embodiments, a single piece of logic provide the described functionality.

As illustrated above, various embodiments for providing a dialog assessment platform are disclosed. These embodiments may improve the accuracy of dialog feedback, as well as improve the efficiency by which customized feedback may be provided. As an example, embodiments may be configured to determine, based on an instructor's past comments, a portion of the dialog that the instructor would likely provide a comments, as well as provide options for template comments. With at least these features, the review process may be quicker, easier, and more accurate.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for providing a dialog assessment platform. It should also be understood that these embodiments are merely exemplary and are not intended to limit the scope of this disclosure.

What is claimed is:

1. A method for providing a dialog assessment platform comprising:
    providing, by a computing device, a first user interface on a dialog training platform for a trainee to practice a skill, wherein the skill includes a dialog interaction between an interviewer and the trainee;
    receiving, by the computing device, a first video recording from the trainee practicing the skill, wherein the first video recording depicts the dialog interaction;
    providing, by the computing device, an option for the trainee to review the first video;
    delaying, by the computing device, providing an option to save the first video by the trainee until the trainee has reviewed the first video, thereby creating an obligation for the trainee to review the first video;
    determining, by the computing device, whether the trainee has reviewed the first video recording via the dialog training platform; and
    in response to determining that the trainee has reviewed the first video recording:
        providing, by the computing device, the first video recording to a trainer;
        providing, by the computing device, a second user interface for the trainer to provide comments to the first video recording;
        receiving, by the computing device, a comment from the trainer at a first section of the first video recording;
        saving, by the computing device, the comment as a previously recorded comment;
        performing, by the computing device, an analysis of the first video recording to determine a feature of the dialog interaction that corresponds to the previously recorded comment;
        predicting, by the computing device, when the trainer will provide the previously recorded comment to a second section of the video recording, based on the analysis of the feature;
        providing, by the computing device, an option to the trainer to insert the previously recorded comment into the second section; and
        in response to selection of the option, inserting, by the computing device, the previously recorded comment at the second section.

2. The method of claim 1, wherein the skill includes at least one of the following: an interview skill, a negotiation skill, a customer service skill, a call center skill, a public speaking skill, a counseling skill, a K-12 skill, a higher education skill, an interpersonal communication skill.

3. The method of claim 1, further comprising:

receiving a second video recording of the trainee;

analyzing the second video recording to predict when the trainer will insert the comment;

in response to determining a third section that the trainer is predicted to insert the comment, providing a second option to insert the previously recorded comment into the third section; and in response to receiving a selection of the second option, inserting the previously recorded comment into the third section.

4. The method of claim 1, in response to determining that the trainee has not reviewed the first video recording, preventing the trainee from submitting the first video recording for trainer review and notifying the trainee of an obligation to review the first video recording.

5. The method of claim 1, wherein the trainer is assigned to review skill practice of a plurality of trainees as part of an organization, and wherein the method further includes providing a third user interface to assign the trainer to the plurality of trainees.

6. The method of claim 1, wherein the trainer provides at least the comment at least once and wherein the method further comprises reviewing substance of all comments provided by the trainer and determining a score for the trainee.

7. The method of claim 6, further comprising tracking progress of the trainee based on the score.

8. The method of claim 1, wherein the comment includes at least one of the following: an audio clip or a video clip.

9. A system for providing a dialog assessment platform comprising:

a processor; and a memory component coupled to the processor, wherein the memory component stores logic that, when executed by the processor, causes the system to perform at least the following:

provide a first user interface on a dialog training platform for a trainee to practice a skill, wherein the skill includes a dialog interaction between an interviewer and the trainee;

receive a first video recording from the trainee practicing the skill, wherein the first video recording depicts the dialog interaction;

provide an option for the trainee to review the first video;

delay providing an option to save the first video by the trainee until the trainee has reviewed the first video, thereby creating an obligation for the trainee to review the first video;

determine whether the trainee has reviewed the first video recording via the dialog training platform;

provide the first video recording to a trainer via the dialog training platform;

provide a second user interface via the dialog training platform for the trainer to provide comments to the first video recording;

receive a comment from the trainer at a first section of the first video recording;

save the comment as a previously recorded comment;

perform an analysis of the first video recording to determine a feature of the dialog interaction that corresponds to the previously recorded comment;

predict when the trainer will provide the previously recorded comment to a second section of the recording, based on the analysis of the feature;

provide an option to the trainer to insert the previously recorded comment into at the second section; and insert the previously recorded comment at the second section.

10. The system of claim 9, wherein the skill includes at least one of the following: an interview skill, a negotiation skill, a customer service skill, a call center skill, a public speaking skill, a counseling skill, a K-12 skill, a higher education skill, an interpersonal communication skill.

11. The system of claim 9, wherein the logic further causes the system to perform at least the following:

receive a second video recording of the trainee;

analyze the second video recording to predict when the trainer will insert the comment;

in response to determining a third section that the trainer is predicted to insert the comment, provide a second option to insert the previously recorded comment into the third section; and in response to receiving a selection of the second option, insert the previously recorded comment into the third section.

12. The system of claim 9, wherein the logic further causes the system, in response to determining that the trainee has not reviewed the first video recording, to prevent the trainee from submitting the first video recording for trainer review and notify the trainee of an obligation to review the first video recording.

13. The system of claim 9, wherein the trainer is assigned to review skill practice of a plurality of trainees as part of an organization, and wherein the logic further causes the system to provide a third user interface to assign the trainer to the plurality of trainees.

14. The system of claim 9, wherein the trainer provides at least the comment at least once and wherein the logic further cause the system to perform at least the following:

review substance of all comments provided by the trainer;

determine a score for the trainee; and track progress of the trainee based on the score.

15. The system of claim 9, wherein the comment includes at least one of the following: an audio clip or a video clip.

16. A non-transitory computer-readable medium comprising logic that, when executed by a computing device performs at least the following:

provide a first user interface via a dialog training platform for a trainee to practice a skill, wherein the skill includes a dialog interaction between an interviewer and the trainee;

receive a first video recording of the trainee practicing the skill;

provide an option for the trainee to review the first video;

delay providing an option to save the first video by the trainee until the trainee has reviewed the first video, thereby creating an obligation for the trainee to review the first video;

determine whether the trainee has reviewed the first video recording via the dialog training platform;

provide the first video recording to a trainer;

provide a second user interface for the trainer to provide recorded comments to the first video recording;

receive a recorded comment from the trainer via the dialog training platform at a first section of the first video recording;

save the recorded comment as a previously recorded comment;

perform an analysis of the first video recording to determine a feature of the interaction that corresponds to the previously recorded comment;

predict when the trainer will provide the previously recorded comment to a second section of the recording, based on the analysis of the feature;

provide an option to the trainer to insert the previously recorded comment into at the second section; and in response to selection of the option, insert the previously recorded comment at the second section.

17. The non-transitory computer-readable medium of claim 16, wherein the skill includes at least one of the following: an interview skill, a negotiation skill, a customer service skill, a call center skill, a public speaking skill, a counseling skill, a K-12 skill, a higher education skill, an interpersonal communication skill.

18. The non-transitory computer-readable medium of claim 16, wherein the logic further causes the computing device to perform at least the following:

receive a second video recording of the trainee;

analyze the second video recording to predict when the trainer will insert the previously recorded comment;

in response to determining a third section that the trainer is predicted to insert the previously recorded comment, provide a second option to insert the previously recorded comment into the third section; and in response to receiving a selection of the second option, insert the previously recorded comment into the third section.

19. The non-transitory computer-readable medium of claim 16, wherein the logic further causes the computing device, in response to determining that the trainee has not reviewed the first video recording, to prevent the trainee from submitting the first video recording for trainer review and notify the trainee of an obligation to review the first video recording.

20. The non-transitory computer-readable medium of claim 16, wherein the trainer is assigned to review skill practice of a plurality of trainees as part of an organization, and wherein the logic further causes the computing device to provide a third user interface to assign the trainer to the plurality of trainees.

* * * * *